US007502115B2

United States Patent
(12) United States Patent
Patel et al.

(10) Patent No.: US 7,502,115 B2
(45) Date of Patent: Mar. 10, 2009

(54) SYSTEM AND METHOD FOR HIGH SENSITIVITY OPTICAL DETECTION OF GASES

(75) Inventors: C. Kumar N. Patel, Los Angeles, CA (US); Michael B. Pushkarsky, Los Angeles, CA (US); Michael E. Webber, Culver City, CA (US); Tyson MacDonald, Los Angeles, CA (US)

(73) Assignee: Pranalytica, Inc., Santa Monica, CA (US)

(*) Notice: Subject to any disclaimer, the term of this patent is extended or adjusted under 35 U.S.C. 154(b) by 57 days.

(21) Appl. No.: 11/986,632

(22) Filed: Nov. 21, 2007

(65) Prior Publication Data

US 2008/0084561 A1 Apr. 10, 2008

Related U.S. Application Data

(62) Division of application No. 11/256,377, filed on Oct. 21, 2005.

(60) Provisional application No. 60/621,099, filed on Oct. 22, 2004.

(51) Int. Cl.
*G01J 3/30* (2006.01)
*G01N 21/00* (2006.01)
*G02B 6/00* (2006.01)

(52) U.S. Cl. ....................... 356/437; 356/432; 356/317; 250/341.2; 250/339.13

(58) Field of Classification Search ......... 356/432–444, 356/311, 315; 250/341.2, 341.6, 339.08, 250/339.13, 339.03
See application file for complete search history.

(56) References Cited

U.S. PATENT DOCUMENTS 3,394,253 A 7/1968 Harrick et al. .............. 250/353
3,820,901 A * 6/1974 Kreuzer ...................... 356/425

(Continued)

FOREIGN PATENT DOCUMENTS

WO WO 2004/104562 12/2004

(Continued)

OTHER PUBLICATIONS

A. Miklos, P. Hess, Z. Bozoki: "Application of acoustic resonators in photoacoustic trace gas analysis and metrology," *Rev. Sci. Inst.* 72(4), 1937—1955 (2001).

(Continued)

*Primary Examiner*—Sang Nguyen
(74) *Attorney, Agent, or Firm*—Cislo & Thomas, LLP

(57) ABSTRACT

A method and apparatus architecture for detecting gases, particularly hazardous gases which should be detected in miniscule amounts. High sensitivity detection of chemical warfare agents (CWAs) is set forth with very low probability of false positives (PFP) by the use of an innovative laser-photoacoustic spectrometer (L-PAS). Detection of diisopropyl methylphosphonate (DIMP), a decomposition product of Sarin and a relatively harmless surrogate for the nerve gases, is made in the presence of other gases that are expected to be interferences in an urban setting. Detection sensitivity for DIMP in the presence of these interferences of better than 0.45 ppb, which satisfies current homeland and military security requirements is shown as well as the first analysis of optical techniques for the detection of chemical warfare agents (CWAs) and toxic industrial chemicals (TICs) in real world conditions.

16 Claims, 13 Drawing Sheets

L-PAS analyzer for CWA detection.

U.S. PATENT DOCUMENTS

| | | | | |
|---|---|---|---|---|
| 4,163,382 | A * | 8/1979 | Amer | 73/24.02 |
| 4,267,732 | A | 5/1981 | Quate | 73/606 |
| 4,492,862 | A * | 1/1985 | Grynberg et al. | 250/255 |
| 4,516,858 | A | 5/1985 | Gelbwachs | 356/437 |
| 4,641,377 | A * | 2/1987 | Rush et al. | 381/111 |
| 4,795,253 | A | 1/1989 | Sandridge et al. | 356/51 |
| 5,241,177 | A | 8/1993 | Albrecht | 250/338 |
| 5,528,040 | A | 6/1996 | Lehmann | 250/343 |
| 6,160,255 | A | 12/2000 | Sausa | 250/227 |
| 6,202,470 | B1 | 3/2001 | Chou | 73/24 |
| 6,527,398 | B1 | 3/2003 | Fetzer | 356/437 |
| 6,618,148 | B1 * | 9/2003 | Pilgrim et al. | 356/432 |
| 6,787,776 | B2 * | 9/2004 | Webber et al. | 250/341.2 |
| 6,862,301 | B2 | 3/2005 | Cox | 372/20 |
| 6,975,402 | B2 | 12/2005 | Bisson et al. | 356/432 |
| 7,004,909 | B1 * | 2/2006 | Patel et al. | 600/532 |
| 7,012,696 | B2 | 3/2006 | Orr et al. | 356/454 |
| 2004/0179200 | A1 | 9/2004 | Yoon et al. | 356/432 |
| 2004/0211900 | A1 | 10/2004 | Johnson | 250/338 |
| 2005/0117157 | A1 | 6/2005 | Tarsa | 356/437 |
| 2005/0207943 | A1 | 9/2005 | Puzey | 422/82 |
| 2006/0043301 | A1 | 3/2006 | Mantele et al. | 250/339 |

FOREIGN PATENT DOCUMENTS

| | | |
|---|---|---|
| WO | WO 2005/088275 | 9/2005 |
| WO | WO 2005/093390 | 10/2005 |
| WO | WO 2006/008557 | 1/2006 |

OTHER PUBLICATIONS

A. O'Keefe and D. A. G. Deacon, "Cavity Ring-Down Optical Spectrometer for Absorption Measurements using Pulsed Laser Sources," *Rev. Sci. Instrum.* 59, 2544-2551(1988).

A. Schmohl, A. Miklos, P. Hess: "Detection of ammonia by photoacoustic spectroscopy with semiconductor lasers," *Appl. Opt.* 41(9), 1815—1823 (2002).

B. McNamara and L. Leitnaker, "Toxicological Basis for Controlling Emission of GB into the Environment" *Edgewood Arsenal Special Publication* (U.S. Army, Medical Research Laboratories, Edgewood Arsenal, Aberdeen Proving Grounds, Maryland. Mar. 1971).

C.K.N. Patel, E.G., Burkhardt, and C.A. Lambert, "Spectroscopic Measurements of Stratospheric Nitric Oxide and Water Vapor," *Science* 184, 1173—1176 (1974).

Department of Health and Human Services, Center for Disease Control, Final Recommendations for Protecting the Health and Safety Against Potential Adverse Effects of Long-Term Exposure to Low Doses of Agents: GA, GB, VX, Mustard Agent (H, HD and T) and Lewisite (L), *Federal Register* 53, 8504-8507 (Mar. 15, 1988).

Department of the Army. *Army Field Manual No. 3-9; Potential Military Chemical/Biological Agents and Compounds*, pp. 19-20. (Headquarters of the Army, Washington, D. C. Dec. 12, 1990).

J. J. Scherer, J. B. Paul, A. O'Keefe and R. J. Saykally, "Cavity Ringdown Laser Absorption Spectroscopy—History, Development and Application to Pulsed Molecular Beams," *Chem. Rev.* 97, 25-51 (1997).

L. B. Kreuzer and C. K. N. Patel, "Nitric Oxide Air Pollution Detection by Optoacoustic Spectroscopy," *Science* 173, 45-47 (1971).

L. B. Kreuzer, "Ultralow Gas Concentration Infrared Absorption Spectroscopy," *J. Appl. Phys.* 42, 2934-2943 (1971).

L.B. Kreuzer, N.D. Kenyon, C.K.N. Patel: "Air Pollution: Sensitive Detection of Ten Pollutant Gases by Carbon Monoxide and Carbon Dioxide Lasers," *Science* 177, 347—349 (1972).

M. B. Pushkarsky, M. E. Webber and C. K. N. Patel, *Appl. Phys. B* 77, 381-385 (2083).

M. B. Pushkarsky, M. E. Webber, T. N. MacDonald and C. K. N. Patel, (*in preparation*).

M. E. Webber, M. B. Pushkarsky and C. K. N. Patel, (*submitted for publication, 2004*).

M. Nagele and M. W. Sigrist, "Mobile laser spectrometer with novel resonant multipass photoacoustic cell for trace-gas sensing," *Appl. Phys. B* 70, 895—901 (2000).

M.B. Pushkarsky, M.E. Webber, and C.K.N. Patel, "Ultra-sensitive ambient ammonia detection using $CO_2$-laser-based photoacoustic spectroscopy," *Appl. Phys. B* 77, 381—385 (2003).

M.B. Pushkarsky, M.E. Webber, O. Baghdassarian, L.R. Narasimhan, and C.K.N. Patel, "Laser-based photoacoustic ammonia sensors for industrial applications," *Applied Physics B* 75 391-396, Sep. 2002.

M.E. Webber, M. Pushkarsky, and C.K.N. Patel, "fiber-amplifier-enhanced photoacoustic spectroscopy with near-infrared tunable diode lasers," *Appl. Opt.* 42(12), 2119—2126 (2003).

P. Hess, Editor: "*Topics incurrent Physics: Photoacoustic, Photothermal and Photochemical Processes in Gases*," Springer-Verlag (1989).

P. Repond and M. W. Sigrist: "Photoacoustic spectroscopy on trace gases with continuously tunable $CO_2$ laser," *Appl. Opt.* 35(21), 4065—4085 (1996).

Peter J. Drivas, Peter A. Valberg, Brian L. Murphy and Richard Wilson, "Modeling Indoor Air Exposure from Short-Term Point Source Releases," *Indoor Air* 6, 271-277 (1996).

Protocol for the Prohibition of the Use in War of Asphyxiating, Poisonous or Other Gases, and of Bacteriological Methods of Warfare (1925); Entry into force: Feb. 8, 1928; The Chemical Weapons Convention was opened for signature in Paris, Jan. 13, 1993 and entered into force Apr. 29, 1997.

S. Schafer, A. Miklos, P. Hess: "Quantitative signal analysis in pulsed resonant photoacoustics," *Appl. Opt.* 36(15), 3202—3211 (1997).

S.W. Sharpe, R.L. Sams, T.J. Johnson, P.M. Chu, G.C. Rhoderick and F.R. Guenther, "Creation of 0.10 $cm^{-1}$ Resolution, Quantitative, Infrared Spectral Libraries for Gas Samples," in SPIE proceedings for Vibrational Spectroscopy-based Sensor Systems, vol. 4577, Nov. 2001, pp. 12-24.

* cited by examiner

IR spectra for CWAs, mustards and TNT.

IR absorption spectra of VX and a potentially interfering species, butyl acetate.

Spectra of nerve agents and $^{12}CO_2$ and $^{13}CO_2$ laser wavelengths

Simulations of 10 ppbv DIMP detection in contaminated air overlaid with the results from measurements of DIMP in clean, dry air.

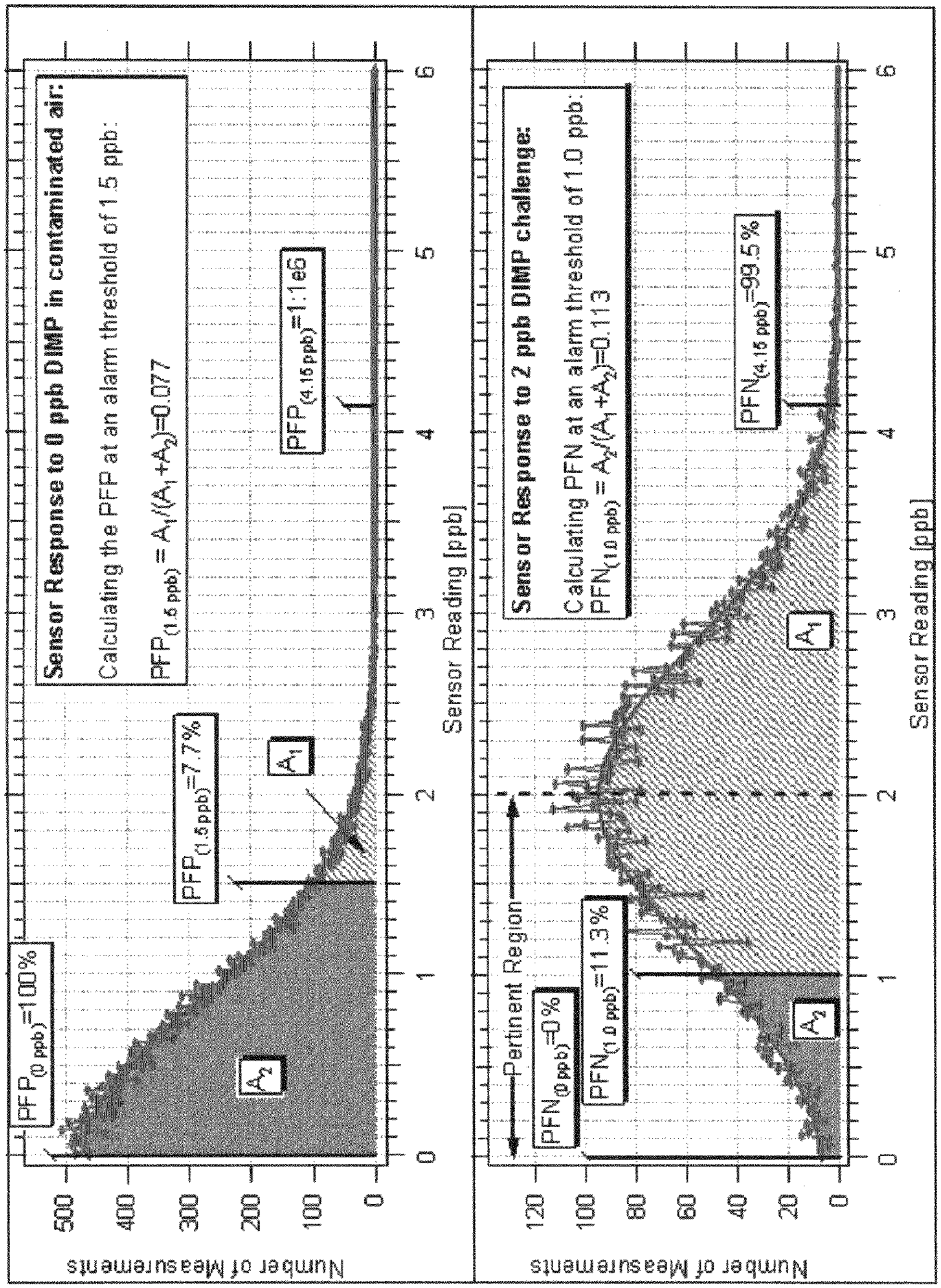

Figure 5

(Top Panel) Simulated sensor response to zero ppb DIMP in contaminated air. The PFP for an alarm threshold of 1.5 ppb is the area A1 divided by the sum of areas A1 and A2.

(Bottom Panel) Simulated sensor response to 2 ppb DIMP in contaminated air. The PFN obtained by analyzing the number of sensor readings that are below a particular alarm threshold even though DIMP is present at higher concentrations.

PFP for simulated measurements of 10 ppbv DIMP in heavily contaminated air. A PFP of $1\times10^{-6}$ is achieved for a detection threshold of 4.15 ppb.

Plot of PFP and PFN vs. detection threshold obtained from simulations.

(Top Panel) Simulated ROC curves illustrating improvement in the PFP of L-PAS detection with improving precision of the sensor (Bottom Panel) Simulations demonstrating the impact of reducing contamination on the performance of the sensor. Typical indoor air has a total VOC (TVOC) density of <0.5 mg/m$^3$ Spectral absorption features of Tabun (GA), Sarin (GB), Soman (GD), Cyclosarin (GF), VX, triethyl phosphate (TEP), dimethyl methylphosphonate (DMMP) and diisopropyl methylphosphonate (DIMP) in the 9-11.5 μm region (top panel); positions and relative power levels of the $^{13}CO_2$ laser output on the lasing transitions as a function of the wavelength (bottom panel).

L-PAS analyzer for CWA detection.

Measured photoacoustic absorption spectra for ammonia, toluene, isopropanol, ethylene, ethanol, methanol, DIMP, and $CO_2$.

L-PAS analyzer measurements: 1) synthetic clean air, 2) Santa Monica city street air, 3) synthetic contaminated air with no DIMP, 4) synthetic contaminated air with 14.3 ppb DIMP present, and 5) synthetic contaminated air with no DIMP.

Measurements of DIMP in synthetic contaminated air and Santa Monica air over 12 hours on different days to determine the sensitivity and PFP

SYSTEM AND METHOD FOR HIGH SENSITIVITY OPTICAL DETECTION OF GASES

CROSS-REFERENCES TO RELATED APPLICATIONS

Applicant(s) and/or Inventor(s) hereby rescind any disclaimer and/or any arguments made in any prior related application. Such disclaimer(s) and/or argument(s) as well as any prior art relevant to such disclaimer(s) and/or argument(s) may need to be revisited by the Examiner.

This patent application is a divisional of U.S. patent application Ser. No. 11/256,377 filed Oct. 21, 2005 entitled SYSTEM AND METHOD FOR HIGH SENSITIVITY OPTICAL DETECTION OF GASES which application is incorporated herein by this reference thereto.

This patent application is related to and claims priority from U.S. Provisional Patent Application Ser. No. 60/621,099 filed Oct. 22, 2004 entitled GAS DETECTOR (aka SYSTEM AND METHOD FOR HIGH SENSITIVITY OPTICAL DETECTION OF GASES) which application is incorporated herein by this reference thereto.

STATEMENT AS TO RIGHTS TO INVENTIONS MADE UNDER FEDERALLY-SPONSORED RESEARCH AND DEVELOPMENT

The United States government may have certain rights to this invention pursuant to DARPA contract no. MDA972-02-C-0092.

COPYRIGHT AUTHORIZATION

Portions of the disclosure of this patent document may contain material which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

BACKGROUND OF THE INVENTION

1. Field of the Invention

This invention relates to the detection of hazardous and/or toxic gases, including warfare gases, and more particularly to a method and apparatus for detecting such gases using optical systems such as laser photoacoustic spectroscopy (LPAS).

2. Description of the Related Art

The terrorist events of Sep. 11, 2001, subsequent anthrax mailings, and the 1995 Tokyo subway Sarin attack by the Aum Shinrikyo cult has heightened worldwide awareness of catastrophic social impact of potential large scale attacks using chemical warfare agents (CWAs), and has exposed the critical need for the reliable, unambiguous and early detection of trace CWAs and toxic industrial chemicals (TICs) in the air. Despite the fact that all countries worldwide are signatories to the Chemical Weapons Convention, which bans the use of CWAs, the U.S. defense establishments have considered their use possible and thus have developed battlefield sensors for the ambient detection of CWAs to protect troops. However, CWA sensors suitable for civilian use in places such as airports, railroads stations, large public and private office buildings, theaters, sports arenas, etc., have received much less attention. Such civilian sensors may require different performance than those deployed in battlefields.

For example, in public settings there is a need for the early detection of CWAs so that parts of buildings can be isolated or evacuated, while a low probability of false positives (PFP) is a necessity to avoid the adverse economic impact caused by false alarms leading to unnecessary evacuations.

A brief background on photoacoustic IR spectroscopy begins with the observation that IR absorption spectroscopy is a powerful tool for trace gas detection because a vast majority of polyatomic molecules, including CWAs, TICs and explosives, absorb light in the wavelength region from 3 to 14 μm. FIG. 1 shows the IR spectra of nerve gases, mustards gases, and TNT, illustrating that the most prominent features for many species of interest lie between 3 and 11.5 μm. Table 1 lists some of the pertinent species that can be detected in different wavelength regions.

TABLE 1

| CWAs, TICs and Explosives that can be Detected in Specific Spectral Regions | |
|---|---|
| | 9-11.5 μm |
| CWAs | Lewisite, Nitrogen Mustard ($H—N_3$), Sulfur mustard (HD), 4-Dithiane, Diisopropyl methylphosphonate (DIMP), Dimethyl methylphosphonate (DMMP), Isoamyl alcohol, Methylphosphonic difluoride (DIFLUOR), Cyclosarin (GF), Sarin (GB), Soman (GD), Tabun (GA), VX, Triethyl phosphate, 2-diisopropylaminoethanol (DIPAE) |
| TICs | Ammonia, Arsine, Boron trichloride, Ethylene oxide, Nitric acid |
| | 4-9 μm |
| CWAs | Mustard ($H—N_3$), Sulfur mustard (HD), 4-Dithiane, |
| TICS | Boron Trifluoride, Carbon Disulfide, Diborane, Formaldehyde, Hydrogen Cyanide, Hydrogen Sulfide, Nitric Acid, Phosgene, Sulfur Dioxide, Tungsten Hexafluoride |
| Explosives | TNT, PETN |
| | 2.5-4 μm |
| TICs | HBr, HCl, HF |

When evaluating an optical detection technology, certain performance characteristics are important and include: sensitivity, specificity, probability of false positives (PFPs) probability of false negatives (PFNs), response time, and recovery time.

Detection sensitivity is a key indicator of overall sensor performance and relates to the minimum gas concentrations that are reliably detected. A good sensitivity enables detecting CWAs or TICs before the concentration rises to dangerous levels, monitoring at low levels for long term exposure problems, and determining when an attack site is safe to reenter.

Specificity, i.e., ability to distinguish between different CWAs, is important to first responders in order to provide appropriate treatments subsequent to the exposure. Specificity yields information not only about how much of a toxic gas is present, but also which gas is present.

Probability of false positives (PFP) provides a number that represents the fraction of measurements that falsely indicate a toxic gas is present when in reality it is not. Such false alarms often arise from interfering gases that might also be present in the indoor or outdoor environment and typically represent the most significant operational difficulty for field-deployed sensors. Very low PFP is desirable since false alarms cause substantial and expensive disruption in the normal routine of those at the measurement site.

Probability of false negatives (PFN) produces a number that reflects the fraction of measurements that falsely indicate a toxic gas is not present even though it is present at or above the set threshold level. A low PFN is desired in order to prevent unknown exposure to toxic air.

Response time relates to near real-time functionality (response time≦60 seconds) which is necessary to provide warnings that are useful for protecting people and evacuating attack sites.

The recovery time parameter reflects the time that a sensor requires to recover from a high reading, whether after an exposure to CWAs and/or TICs or a false reading prompted by the presence of an interfering gas.

Designing a sensor to simultaneously satisfy these standards requires a quantitative understanding of the sensor's operational characteristics as well as the nature of interferences expected in realistic environment and their impact on the sensor's operational characteristics.

The required sensitivity for CWA detection can be determined by the toxicity levels of particular agents, most of which have been reasonably well documented. With the 1995 Tokyo scare, Sarin (GB), a typical nerve agent CWA, has received interest within the scientific community; the concentrations and related health effects for it are summarized in Table 2.

TABLE 2

Summary of Allowable Sarin Dose for Different Health Effects

| Health Effect | Dose | Remarks |
|---|---|---|
| Lethal (50%) | 100 mg-min/$m^3$ | Resting |
| Incapacitation (50%) | 75 mg-min/$m^3$ | Resting |
| Miosis | 1 mg-min/$m^3$ | |
| Occupational Limit | 48 μg-min/$m^3$ | 8 hour/day, 40 hours/week, 40 years |
| General Population | 12.96 μg-min/$m^3$ | |

For a 30 minute exposure to Sarin, the lethal concentration is approximately 575 parts-per-billion (ppb), or 3.3 mg/$m^3$, while the first noticeable health effect (miosis) occurs at 33.3 μg/$m^3$ (5.8 ppb). For the general population, the suggested limit would be 27 ng/$m^3$ (4.7 ppt) for an 8 hour exposure. Thus, to protect population from harm in the event of a Sarin attack, reasonable design targets for CWA sensors include 1) a sensitivity of approximately 1 ppb (well below the harm threshold for 30-minute exposure), and 2) a measurement time shorter than 1 minute to allow reasonable time for evacuation. The thresholds for harm from the other CWAs are similar.

The CWAs have absorption strengths of ~3-6×$10^{-3}$ [ppm.meter]$^{-1}$ (FIG. 1). For illustration, VX may be used as a typical CWA, having a peak absorption of 2×$10^{-3}$ [ppm.meter]$^{-1}$ at 9.6 μm. Consequently, the infrared absorption at 9.6 μm from 1 ppb of VX would be 2×$10^{-8}$ $cm^{-1}$. Thus, detecting typical CWAs at ppb and sub-ppb levels using optical absorption techniques requires an absorption measurement capability as low as $10^{-8}$ $cm^{-1}$.

Though sensitivity is a key parameter for a trace gas detection sensor, it is the selectivity (the ability to discriminate the target from interferences to avoid false alarms) that becomes the limiting performance factor when the sensors are used in real-world settings. In these environments, the ambient air can often be heavily contaminated with potential interferences.

Traditionally, absorption spectroscopy sensors avoid the effect of interferences by measuring absorption either at a single wavelength or over narrow wavelength region where the target gas absorbs, but the other gases in the sample do not absorb. This approach has been successful for the detection of smaller molecules in relatively clean samples, where the target spectra are sharp and the potential interferences are minimal. However, because CWAs and a majority of interferences that occur in realistic air samples are relatively large polyatomic molecules, their IR spectra are characterized by broad absorption features as seen from FIG. 2 that shows the infrared absorption spectrum of VX and an interference, butyl acetate. The spectra are several hundred nanometers wide, which is typical of CWAs and interferences, and overlap significantly between 9.5 and 9.9 μm. Since the targets and interferences absorb the probe light at many of the same wavelengths, selective spectroscopic detection of the target requires the acquisition of the spectrum over a broad wavelength range followed by quantitative decomposition into the contributing spectral signatures of the targets and interferences. Thus absorption sensors that operate over a narrow wavelength range would not be able to adequately distinguish these two species.

A sensor's selectivity is typically explained quantitatively through the PFP (or false alarm rate). For a sensor that has a one-minute measurement time, a reasonable design target is to achieve a PFP less than 2×$10^{-6}$, which corresponds to a false alarm rate of <1 per year. The design targets for 10 second and 1 second measurement times would be a PFP of 3×$10^{-7}$ and 3×$10^{-8}$, respectively in order to keep the false alarm rate at less than 1 (one) per year.

As described above, sensors need to detect absorptions as small as $10^{-8}$ $cm^{-1}$. There are a number of optical techniques that permit measurements of such small absorptions, the most common of which are long path absorption measurements (e.g., multipass cells and cavity ring-down spectroscopy) and calorimetric techniques (e.g., photoacoustics).

SUMMARY OF THE INVENTION

In view of the foregoing disadvantages inherent in the known types of gas detectors now present in the prior art, the present invention provides a new methodology and architecture for gas detectors wherein gases, particularly hazardous gases, can be detected and determined.

The general purpose of the present invention, which will be described subsequently in greater detail, is to provide gas detection technology which is not anticipated, rendered obvious, suggested, taught, or even implied by any of the prior art gas detectors, either alone or in any combination thereof.

Problems arise in the detecting of a target species in the presence of a multitude of interferences that are often are stochastic. Provided is a broadly applicable technique for evaluating the sensitivity, probability of false positives (PFP) and probability of false negatives (PFN) for a sensor through the illustrative example of a laser photoacoustic spectrometer (L-PAS). This methodology includes: 1) a model of real-world air composition, 2) an analytical model of an actual field-deployed L-PAS, 3) stochasticity in instrument response and air composition, 4) repeated detection calculations to obtain statistics and receiver operating characteristic (ROC) curves, and 5) analyzing these statistics to determine the sensor's sensitivity, PFP and PFN. This methodology was used to analyze variations in sensor design and ambient conditions, and can be utilized as a framework for comparing different sensors.

The simulation model developed to evaluate the sensor performance, includes a model of realistically contaminated air, a model of actual sensor performance, and quantitative spectral libraries. The results of an L-PAS sensor performance simulation for CWA detection are set forth with the analysis extended to predict performance of notional sensors with different operational characteristics and different levels of air contamination, thus, providing "scaling laws" for optical sensors and permitting sensor performance evaluations in extreme situations.

Using laser photoacoustic spectroscopy (L-PAS) as an example, optical techniques may be used for the detection of CWAs (chemical warfare agents) and TICs (toxic industrial chemicals) by explicitly incorporating the stochastic nature of sensor noise characteristics and interferences in a real world situation. Based on a model developed to simulate an actual trace gas sensor, theoretical receiver operational characteristic (ROC) curves may be determined, which include quantitative sensitivity, selectivity, PFP and PFN as a function of instrument noise characteristics, spectrometer spectral coverage, and air composition. Thus, a universal road map for optimizing the performance of trace gas sensors in the presence of interferences and for performing useful intercomparisons of different techniques is provided.

L-PAS (laser-photoacoustic spectroscopy) (as one of possibly many alternatives) illustrates the analytical methodology by 1) simulating real-world air that represents a complicated mix of potential interferences, 2) creating an analytical model of the L-PAS sensor, 3) incorporating stochasticity to the model by adding random noise proportional the instrument's precision and varying interference concentrations, 4) simulating the operation of the sensor model by performing repeated sample calculations to yield useful statistics and ROC curves, and then 5) analyzing these statistics to determine the sensor's replicate precision (sensitivity), PFP (selectivity), and PFN (reliability).

In this way, an improved gas detector may be provided generally along the lines of the optical/electromagnetic frequency regimes available.

In one embodiment, a gas detector has an optical analyzer detecting in a sample of gas optical absorbance of the sample at a plurality of wavelengths. The optical analyzer then transmits an absorbancy signal representative of optical absorbancy for each respective one of the plurality of wavelengths. A spectral library of gas species absorbing one or more of the plurality of wavelengths is provided that includes determined absorptions for expected gases and target gases. In conjunction with this library, a processor receives the absorbancy signals from the optical analyzer and applies pattern recognition (such as least squares fitting) using the absorbancy signals and the determined absorptions to provide mole fraction quantities for each of the expected gases and each of the target gases. In this way, the sample of gas may be analyzed for presence and quantity of expected gases and target gases.

In another embodiment, a high sensitivity gas detector for detection of hazardous gases with reduced probability of false positive and false negative signals uses a light source transmitting modulated tunable radiation to illuminate a photoacoustic test cell. The photoacoustic test cell has a microphone system that transmits a photoacoustic signal to a signal receiver that receives the microphone signal. The signal receiver transmits a normalized signal to a signal processor which analyzes the normalized signal in conjunction with at least one entry in a library for signal signatures for gases detectable by the radiation. The signal processor transmits a resulting signal indicating a quantity of the hazardous gases in the test cell. In this way, detection of known hazardous gases can be made by illuminating sample air or other gas in the photoacoustic test cell.

In a further embodiment, a method for detecting gases is set forth herein that includes the initial step of providing a gas sample to be tested. An optical analyzer is provided that transmits a signal proportional to optical absorbance. The step of analyzing the gas sample with the optical analyzer to obtain an absorbancy signal is then performed. The absorbancy signal for the gas sample as a whole is then analyzed in conjunction with a spectral library of determined absorptions for expected gases and target gases. The mole fractions for the expected gases and the target gases is then determined. In this way, the gas sample may be analyzed for presence and quantity of expected gases and target gases. Generally, such expected gases are those of the air ambient the detector which are usually the same from day to day and so can generally be determined in advance. The target gases are those hazardous ones which could be expected from either a foe or adversary in the case of chemical warfare agents (CWAs) or explosives, or from an industrial accident in the case of toxic industrial chemicals (TICs).

The technology set forth herein is generally not hampered by a large spectral library as the same can be contained on an updatable chip, EEPROM, or the like. The same could be updated in all ways now known or later developed so that a central laboratory could update units in the field, battlefield or otherwise. The anticipated development of low-energy high-capacity microprocessors could provide a universal gas detector and/or provide the basis for gas detection based upon optical detection of the chemical bonds present in the gas and constructing mathematically or otherwise the resulting molecules from the detected chemical bonds.

BRIEF DESCRIPTION OF THE DRAWINGS

FIG. 5 (top panel) is a sensor reading of a simulated sensor response to zero ppb DIMP in contaminated air. The PFP for an alarm threshold of 1.5 ppb is the area $A_1$ divided by the sum areas $A_1$ and $A_2$. The bottom panel is a sensory reading of a simulated sensor response to 2 ppb DIMP in contaminated air. The PFN is obtained by analyzing the number of sensor readings that are below a particular alarm threshold even though DIMP is present at higher concentrations and this case (where the threshold level is 1 ppb), the PFN is the area $A_2$ divided by the total area under the curve ($A_1+A_2$).

DESCRIPTION OF THE PREFERRED EMBODIMENT(S)

Figure 1:
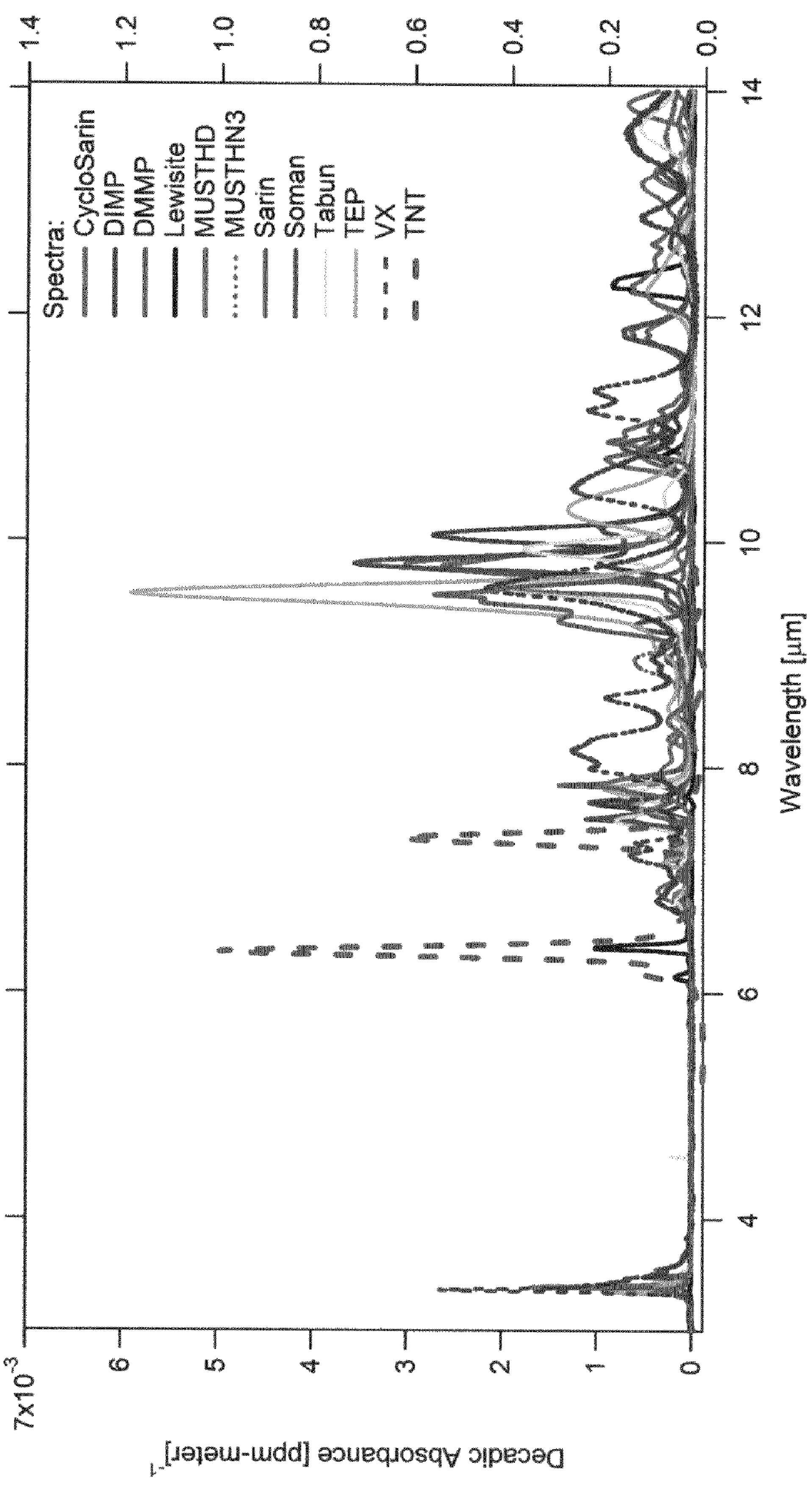
FIG. 1 is a graph of IR spectra for CWAs, mustards, and TNT.
Figure 2:
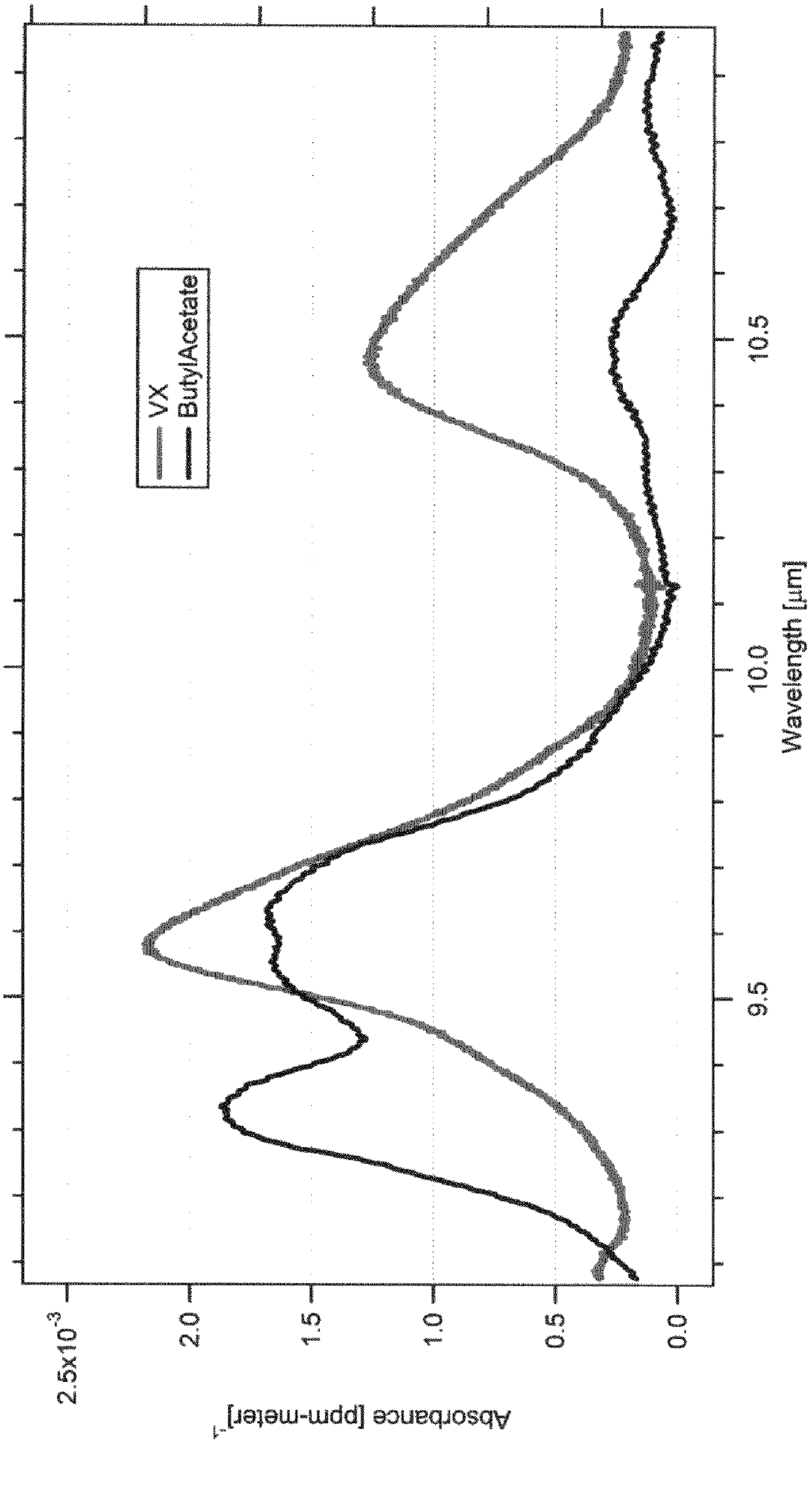
FIG. 2 is a graph of IR absorption spectra of VX and a potentially interfering species, butyl acetate.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

As set forth herein, the use by example of L-PAS is advantageous because reliable instruments based on this technique are commercially available for ppb (parts per billion) and sub-ppb detection of a variety of relevant trace gases and because it meets important sensitivity requirements.

However, a wide variety of optical detection techniques, instrument, and devices may be advantageously used in conjunction with the present system and method. These include: tunable laser systems; laser photoacoustic systems including a L-PAS system using a $CO_2$ laser; long path optical absorption measuring systems; cavity ring-down spectroscopy systems; FTIR systems; a L-PAS using one or several tunable quantum cascade lasers; a L-PAS using a tunable parametric oscillator; a L-PAS using one or several direct bandgap recombination type semiconductor lasers; a L-PAS using any combination of $CO_2$ lasers, quantum cascade lasers, parametric oscillators, and direct bandgap recombination type semiconductor lasers; a tunable $CO_2$ laser; a tunable $CO_2$ laser tunable to wavelengths inclusively between 9.0 μm and 11.5 μm; one or more tunable quantum cascade lasers; a tunable quantum cascade laser tunable to wavelengths inclusively between 3.0 μm and 15 μm; a tunable parametric oscillator; a tunable parametric oscillator tunable to wavelengths inclusively between 2.0 μm and 15 μm; one or more tunable direct bandgap recombination type semiconductor lasers; a tunable direct bandgap recombination type semiconductor laser tunable between wavelengths inclusively between 1.0 μm and 15 μm; any combination of $CO_2$ lasers, quantum cascade lasers, parametric oscillators, and direct bandgap recombination type semiconductor lasers; any tunable combination of $CO_2$ lasers, quantum cascade lasers, parametric oscillators, and direct bandgap recombination type semiconductor lasers, such tunable combination tunable between wavelengths inclusively between 1.0 μm and 15 μm; and any combinations of the foregoing.

L-PAS is often used with high-power $CO_2$ lasers that provide 1) wide tunability necessary for measuring CWAs in the presence of interferences (interfering agents/chemicals/gases), 2) high resolution for distinguishing sharp spectral features, and 3) spectral overlap with the wavelength region where most CWAs and many TICs absorb. Though L-PAS is used for illustrative purposes, the analysis and disclosure presented here is independent of the specific absorption measurement technique.

Specifically, L-PAS involves absorption of the modulated laser radiation followed by deactivation of the excited molecule via collisions, which convert the absorbed energy into periodic local heating at the modulation frequency, and generate acoustic waves that can be monitored using low-noise microphones.

The photoacoustic signal, S, in volts is:

$$S=S_m PC\alpha, \tag{1}$$

where the microphone sensitivity, $S_m$, is in units of volts per Pascal; the power, P is in watts; the absorption coefficient $\alpha$ is in $cm^{-1}$; and the cell factor, C, has units of Pascal per inverse centimeters per watt. The photoacoustic signal is linearly proportional to the incident laser power and absorption coefficient at the laser wavelength. Thus, photoacoustic detection of trace gases derives sensitivity benefit from the use of as much laser power as is appropriate. To first order, L-PAS is a zero baseline technique (i.e., if no gases are present to absorb the light, then the transducer yields no signal) and is typically linear over 5 orders of magnitude, and thus shows magnificent dynamic range.

A model of a tunable $CO_2$ laser L-PAS sensor was created using (1) characteristics of an actual field-deployed unit and the spectral information of relevant CWAs, TICs and (2) potential interferents that might be present. This model was then used repeatedly to simulate CWA detection in the presence of interferences to yield statistics that could be used to estimate the L-PAS sensor's sensitivity, PFN and PFP. The model incorporates the stochastic nature of sensor instrumentation by adding appropriate noise to the simulated L-PAS spectrum, while the stochastic nature of the interference composition is accounted for by varying the calculated contamination in different air samples. The model presented herein simulates sensor performance as a function of three parameters:

1) Spectral range available from the laser;

2) The stochastic noise characteristics of an actual L-PAS sensor, including floor noise, precision, and integration time; and 3) List of targets and probable interferences with their expected concentrations and their quantitative spectra (i.e., the spectral libraries).

The sensor model uses actual performance characteristics of a practical field instrument that measures ambient ammonia in the presence of interferences using a line tunable $CO_2$ laser based L-PAS sensor. This sensor uses a $^{13}CO_2$ laser with 5 W of average output power operating on its 10R(18) transition near 10.784 μm to interrogate ammonia's strong $^{Q}Q_6(6)_a$ transition. Interferences from $CO_2$, $H_2O$ continuum and window absorptions are subtracted by switching to neighboring laser lines, yielding a replicate precision of 32 ppt. This detectivity corresponds to a minimum detectable fractional absorbance of $8.8\times10^{-9}$, and a minimum detectable absorption coefficient of $9.6\times10^{-10}$ $cm^{-1}$, thereby satisfying sensitivity requirements. The line-switching algorithm can be extended over many laser lines and combined with linear (and possibly other) pattern recognition techniques to detect many species in the presence of a vast majority of interferences encountered in contaminated or indoor air. From measurements with clean air we derive the stochastic instrument noise to be 0.2% of the signal amplitude.

Because interferences are an important part of actual sensor performance in the field, realistic measurement conditions are simulated by developing a model of heavily contaminated air that contains a number of trace constituents of anthropogenic and biogenic origin. For example, outdoor air, even in unpolluted areas contains $CH_4$, higher alkanes, $NO_x$, $SO_x$, $NH_3$, $O_3$, CO and $CO_2$. Urban polluted air contains fuel vapors, numerous VOCs (volatile organic chemicals) resulting from incomplete combustion in car engines and smoke stack emissions, as well as an array of intermediates resulting from their atmospheric degradation. Rural air may be contaminated by emissions from agricultural operations leading to significant concentrations of ammonia and sulfur-containing compounds. The sources of indoor air contamination are even more diverse and include cleaning agents, products of out gassing of common construction materials, paints, solvents, perfumes, food, and tobacco smoke.

Since there is no single reference source that comprehensively quantifies realistic air constituents, an exhaustive list of documented pollutants was compiled. Where both mean and instantaneous (spike) concentration levels are reported in the literature, the higher spike values were chosen to be representative of the highest possible contamination and to serve as a stricter test. For most chemicals, however; only average values over multi-hour measurement periods are available. To estimate the highest possible spike values, resulting from spills, use is made of the results of an analytical model, which considers a vapor diffusion process from a point source in a reasonably ventilated indoor area. According to this model, the highest concentration reached in the vicinity (one meter away) of the spill is 4 (four) times the steady-state value established after the evaporation rate becomes equal to the rate of removal of the vapor via ventilation. Therefore, in the cases where only mean concentrations were reported, we multiplied the highest reported value by a factor of four to achieve the expected spike value. The list includes more than 300 species and represents, possibly, the most complete compilation of published data on the topic and, thus, is the best practical starting point for evaluating a sensor's performance in realistic air. The complete list of documented compounds, their largest reported concentrations, and references to original literature sources are not reported here, but may be obtained from publicly-available sources. We have also assembled a digital quantitative, high resolution (0.25 $cm^{-1}$) library of absorption spectra of each of these potential interferences by using published databases and commercially available databases.

This list of some three hundred species is impractically large and is truncated for the present analysis by removing a chemical from further consideration if:

it has been reported in indoor air in negligible quantities such that its optical absorption is less than the equivalent of 1 ppb of Sarin. 1 ppb of Sarin is used as a cutoff since this number is well below the harm threshold of 5.8 ppb for a 30 minute exposure as seen above, and if the species does not absorb light appreciably at any wavelength within the range of the carbon dioxide laser, and therefore would not interfere with a target gas even if present in substantial quantities.

Table 3 lists 45 species that meet the criteria and are part of the interference library.

TABLE 3

$^{13}CO_2$ laser based L-PAS sensor interference list

| Species | Concentration [ppb] |
|---|---|
| H2O | 4.00E+07 |
| EthyleneGlycol | 491 |
| Toluene | 2382 |
| CO2 | 550000 |
| Ethanol | 146 |
| Ammonia | 22 |
| Isopropanol | 212 |
| Methanol | 16 |
| pXylene | 649 |
| AceticAcid | 92 |
| mXylene | 649 |
| Ethylbenzene | 252 |
| EthylAcetate | 16 |
| Texanol | 25 |
| ButylAcetate | 14 |
| Formaldehyde | 400 |
| Ozone | 15 |
| TCTFE | 3 |
| pDCB | 13 |
| Butanol | 21 |
| 2Butoxyethanol | 15 |
| 2Ethylhexanol | 8 |
| Benzene | 34 |
| Trichloroethane | 148 |
| Styrene | 14 |
| Naphthalene | 71 |
| Ethylene | 10 |
| Chloroethane | 20 |
| Acrylonitrile | 11 |
| Propylene | 10 |
| aPinene | 60 |
| Acrolein | 11 |
| 2Butanone | 42 |
| Freon12 | 370 |
| Isobutanol | 2 |
| TMB | 17 |
| dLimonene | 23 |
| 13Butadiene | 5 |
| oDCB | 2 |
| MTBE | 13 |
| Butane | 33 |
| Freon11 | 28 |
| oXylene | 16 |
| EEACET | 2 |
| Chloroform | 38 |

Figure 3:
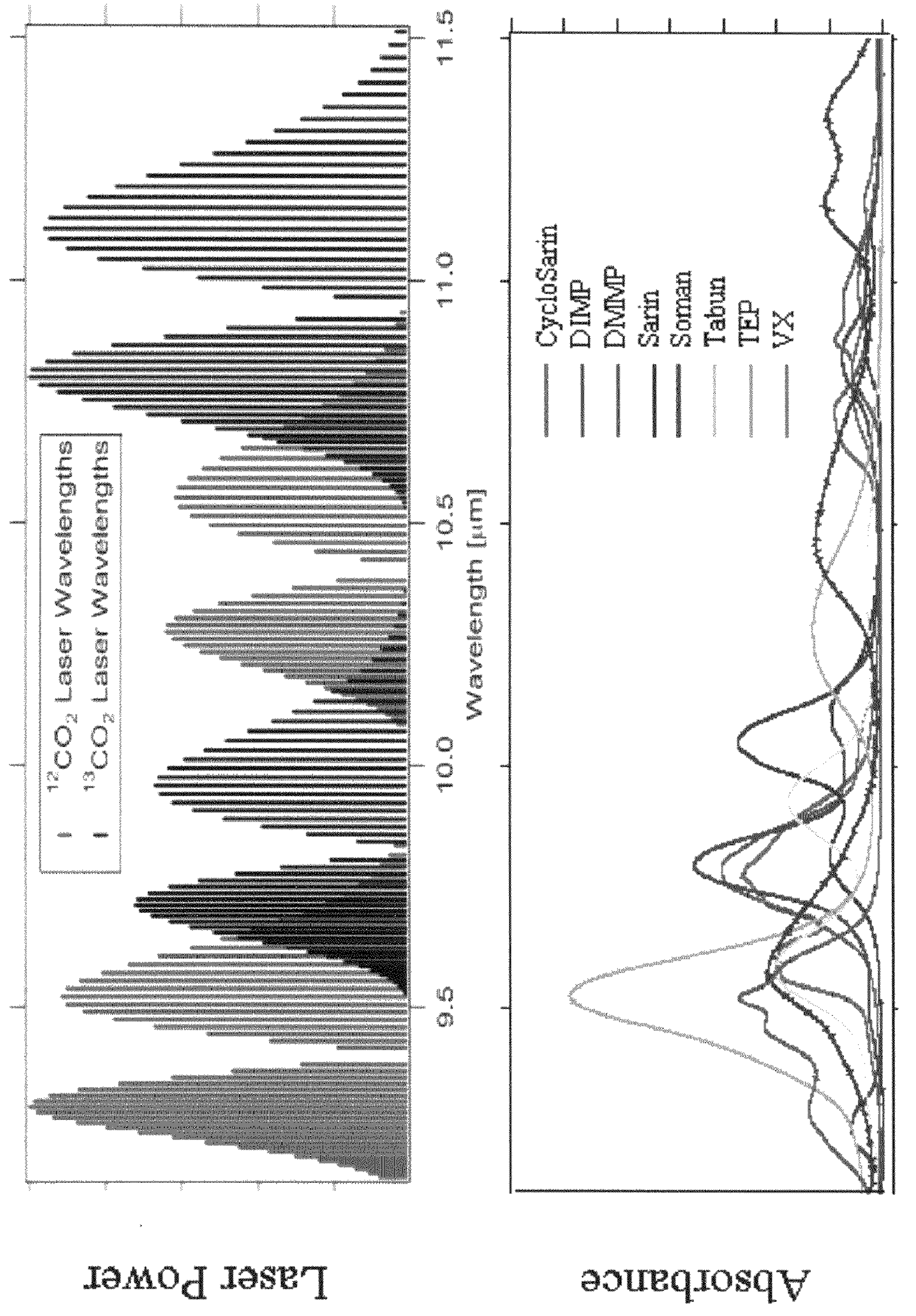
FIG. 3 is a spectra of nerve agents and $^{12}CO_2$ and $^{13}CO_2$ laser wavelengths.

FIG. 3, showing the absorption spectra of eight target nerve agents and surrogates at wavelengths accessible with $^{12}CO_2$ and $^{13}CO_2$ lasers, indicates that the spectrum of DIMP (a surrogate for nerve agents) has excellent overlap with the $^{13}CO_2$ laser. Consequently, the modeling was performed for a $^{13}CO_2$ laser L-PAS sensor for DIMP detection. The libraries of spectra were converted into the spectra specific to a $^{13}CO_2$ L-PAS by evaluating the absorption coefficients at the 87 discrete $^{13}CO_2$ laser wavelengths in the 9.6-11.5 μm range. The spectral signatures of the 46 interferents were then used to evaluate matrix elements involved in the least squares fit (LSF) spectral decomposition as described herein.

In realistic air, both targets and interferents contribute to the measured L-PAS spectrum. The mathematical problem of decomposition of multi-component spectrum may be solved using the least square fitting (LSF) technique.

$$S=S_m PC\alpha \quad (1)$$

Using Equation 1, a L-PAS spectrum of the air containing multiple contaminants can be simulated.

In the gas mixture the absorption coefficient, $\alpha_{\lambda_i}$, at each wavelength is given by, $$\text{Absorption Coefficient}|_{\lambda_j} = \alpha_{\lambda_j} = \sum_{i=1}^{\#species} \alpha_{i,\lambda_j} = \sum_{i=1}^{\#species} X_i * \sigma_{i,\lambda_j} \quad (2)$$

where $\sigma_{i,\lambda_j}$ is the absorbance for species i at wavelength $\lambda_j$, and $X_i$ is the mole fraction of the species i. According to Equation 1, if $S_{\lambda_i}$ is the measured photoacoustic signal and $P_{\lambda_i}$ is the measured laser power at given wavelength, the L-PAS spectrum (the set of values of absorption coefficients, $\alpha_{80_j}$ vs. wavelength, $\lambda_j$) may be obtained using Equation 3:

$$\alpha_{\lambda_j measured} = \frac{S_{\lambda_j}}{S_m P_{\lambda_j} C} \quad (3)$$

Combining Equation 2 and Equation 3, and noting that in any real sensor a measured absorption coefficient, $\alpha_{\lambda_j measured}$ inevitably contains instrumentation noise, yields:

$$\alpha_{\lambda_j measured} = \sum_{i=1}^{\#species} X_i * \sigma_{i,\lambda_j} + Noise_{\lambda_j} \quad (4)$$

The L-PAS spectrum of a multi-component mixture is a linear combination of the known spectra of in individual constituents, with the coefficients being the mole fractions of individual components, $X_i$, plus a stochastic term due to instrumental noise of the sensor. During measurements, the sensor acquires an L-PAS spectrum of a sample. The unknown mole fractions for each species are subsequently determined via the linear list square fit, i.e., from the requirement that the sum of squares of the differences between measured and simulated absorption coefficients (so-called merit function, $\chi^2$) over all wavelengths is minimum:

$$\chi^2 = \sum_j^{\#lines} \left( \alpha_{\lambda_j measured} - \sum_{i=1}^{\#species} X_i * \sigma_{i,\lambda j} \right)^2 = \min \quad (5)$$

Using vector-matrix notation Equation 4 may be represented as:

$$\overbrace{\begin{bmatrix} \sigma_{\lambda_1,1} & \sigma_{\lambda_1,2} & \cdots & \sigma_{\lambda_1,M} \\ \sigma_{\lambda_2,1} & \sigma_{\lambda_2,2} & \cdots & \sigma_{\lambda_2,M} \\ \vdots & \vdots & \ddots & \vdots \\ \sigma_{\lambda_N,1} & \sigma_{\lambda_N,2} & \cdots & \sigma_{\lambda_N,M} \end{bmatrix}}^{Spectral\ Coefficients} \overbrace{\begin{Bmatrix} X_1 \\ X_2 \\ \vdots \\ X_M \end{Bmatrix}}^{Molefractions} + \overbrace{\begin{Bmatrix} n_1 \\ n_2 \\ \vdots \\ n_M \end{Bmatrix}}^{Noise} = \overbrace{\begin{Bmatrix} \alpha_1 \\ \alpha_2 \\ \vdots \\ \alpha_M \end{Bmatrix}}^{Measured\ Absorbance} \quad (6)$$

The LSF values of individual mole fractions, Xi, which are the solutions of Equation 5 are given by Equation 7:

$$\overbrace{\begin{Bmatrix} X_1 \\ X_2 \\ \vdots \\ X_M \end{Bmatrix}}^{Molefractions} = \begin{bmatrix} \vec{\sigma}_1\vec{\sigma}_1 & \vec{\sigma}_2\vec{\sigma}_1 & \cdots & \vec{\sigma}_N\vec{\sigma}_1 \\ \vec{\sigma}_1\vec{\sigma}_2 & \vec{\sigma}_2\vec{\sigma}_2 & \cdots & \vec{\sigma}_N\vec{\sigma}_2 \\ \vdots & \vdots & \ddots & \vdots \\ \vec{\sigma}_1\vec{\sigma}_M & \vec{\sigma}_2\vec{\sigma}_1 & \cdots & \vec{\sigma}_N\vec{\sigma}_M \end{bmatrix}^{-1} \overbrace{\begin{bmatrix} \sigma_{\lambda_1,1} & \sigma_{\lambda_2,1} & \cdots & \sigma_{\lambda_N,1} \\ \sigma_{\lambda_1,2} & \sigma_{\lambda_2,2} & \cdots & \sigma_{\lambda_N,2} \\ \vdots & \vdots & \ddots & \vdots \\ \sigma_{\lambda_1,M} & \sigma_{\lambda_2,M} & \cdots & \sigma_{\lambda_N,M} \end{bmatrix}}^{Spectral\ Coefficients} \overbrace{\begin{Bmatrix} \alpha_1 \\ \alpha_2 \\ \vdots \\ \alpha_M \end{Bmatrix}}^{Measured\ Absorbance} \quad (7)$$

The LSF algorithm for an ideal sensor (with zero noise), yields the concentration of the target species even in the presence of multiple interferences if: 1) a quantitative L-PAS spectral library for all expected targets and interferences exists, 2) the number of wavelengths used for the measurement is greater than the number of absorbing species and 3) the individual spectra are linearly independent. A stochastic noise term in Equations 5 and 6 introduces error in the measured absorption coefficients and consequently in the best-fit values of Xi as obtained from Equation 7. Sensor model simulations based on Equations 4-7, described below, reveal quantitative limitation imposed by stochastic noise on the performance of practical sensors.

To quantitatively analyze the performance of L-PAS for CWA detection (sensitivity, specificity, PFN and PFP), one needs to understand the sources and evaluate the magnitude of noise in the detection scheme of the actual L-PAS based instrumentation. The L-PAS sensor has two critical transducers that introduce noise; a microphone (or microphone system) measuring the photoacoustic signal, $S_{\lambda_j}$, and a power meter measuring the laser power, $P_{\lambda_j}$. Outputs from these two sensors are used to obtain the absorbance values, $\alpha_{\lambda_j}$, using Equation 2. For constant ambient conditions (temperature, pressure) of the sample in the photoacoustic cell, the uncertainty in the measured absorption coefficient arises from the sensor noise.

The sensor noise is a sum of noise independent of signal amplitude (the floor noise) and noise proportional to the total measured PAS signal amplitude scaled by the instrument precision, β.

$$\text{Noise} = \sqrt{n_{floor}^2 + n_{precision}^2} \quad (8)$$

$$n_{precision} = \alpha_{\lambda_j} \times \beta \quad (9)$$

The fundamental noise floor on photoacoustic detection arises from the Brownian noise created by the gas molecules in the photoacoustic sensor and is given by an equivalent absorbed optical power of about $10^{-11}$ W $Hz^{-1/2}$ at room temperature. For actual instruments, the lowest possible floor noise value is determined by the specifications of the transducers, i.e., the power meter and the microphone. The instrument precision is, in turn, determined by the quality, i.e., linearity, digitization resolution, etc. of the signal conditioning and data acquisition electronics. Floor noise and the precision values were determined from a field deployed L-PAS sensor, and, yielded a precision of approximately β=0.002 with roughly Gaussian stochastic properties and no obvious systematic components. At this level, the precision noise exceeds the floor noise by almost three orders of magnitude and the latter can thus be disregarded.

Thus, an absorption spectrum of an air sample containing a particular mixture of trace gases (both targets and interferences) acquired with $CO_2$ L-PAS sensor may be simulated using Equation 4 with the noise term governed by limited sensor precision:

$$\alpha_{\lambda_j} = \sum_{i=1}^{\#species} X_i \cdot \sigma_{i,\lambda_j} \cdot (1 + \beta \cdot gauss) \tag{10}$$

where β is the sensor precision, and gauss is the function generating Gaussian-distributed random numbers with a mean value of 0 and variance (one standard deviation) of 1. If there is no instrumental noise, β=0, i.e., no stochasticity, the best fit values, $X_i$ best-fit, practically coincide with the values of $X_i$, used to simulate air in Equation 10. As the stochastic instrumental noise is added, the LSF produces values of $X_i$ best-fit which differ from the value $X_i$ from Equation 10. The statistical distribution of this difference allows one to quantitatively measure the sensor performance.

Simulations can, now, be performed using the analytical model to predict the PFN, PFP and sensitivity for the sensor. The steps leading to the generation of ROC curves are:

Generate a synthetic photoacoustic spectrum of the "contaminated air" by adding up the absorption spectra of all interferents at their highest concentrations and imposing a stochastic noise according to Equation 10.

Determine the best-fit mole fraction of a particular target species (DIMP), $X_{DIM\text{-}best\ fit}$, by the LSF analysis of the synthetic spectrum using Equation 7 (with all involved matrix elements evaluated using the absorbance values $\sigma_{i,\lambda_j}$ from spectral library).

Repeat the simulation large number of times (~$10^5$), each time generating different spectrum due to stochastic nature of the gauss function. The resulting distribution of the best-fit concentration values, $X_{DIMP\text{-}best\ fit}$, yields instrument sensitivity, PFP, and PFN versus detection threshold and challenge respectively.

The simulation was first performed for the case of 10 ppbv DIMP challenge in clean, dry air yielding a histogram of results with a deduced average measurement of 10.00 ppbv and a standard deviation of 20 ppt. These results agree well with the field sensor tests for ammonia, which has a similar peak absorption coefficient as DIMP. The simulation for 10 ppbv DIMP was repeated with interferences from a worst-case air model (Table 4), including high humidity (4% $H_2O$), 550 ppm $CO_2$, and high VOC density of 23.7 mg/$m^3$, which is nearly two orders of magnitude greater contamination than that in nominal conditions. For this simulation, the average deduced value is 10.00 ppbv with a standard deviation of 840 pptv, illustrating that the impact of the interfering species. The histograms of results for the two simulations are overlaid in FIG. 4. The impact of the interferences on the measurement precision is due to the increased absorption coefficients measured by the sensor leading to an increase in their absolute uncertainty due to limited instrumental precision (Eq. 10), which leads to an increased uncertainty in the results of the spectral decomposition algorithm.

Figure 4:
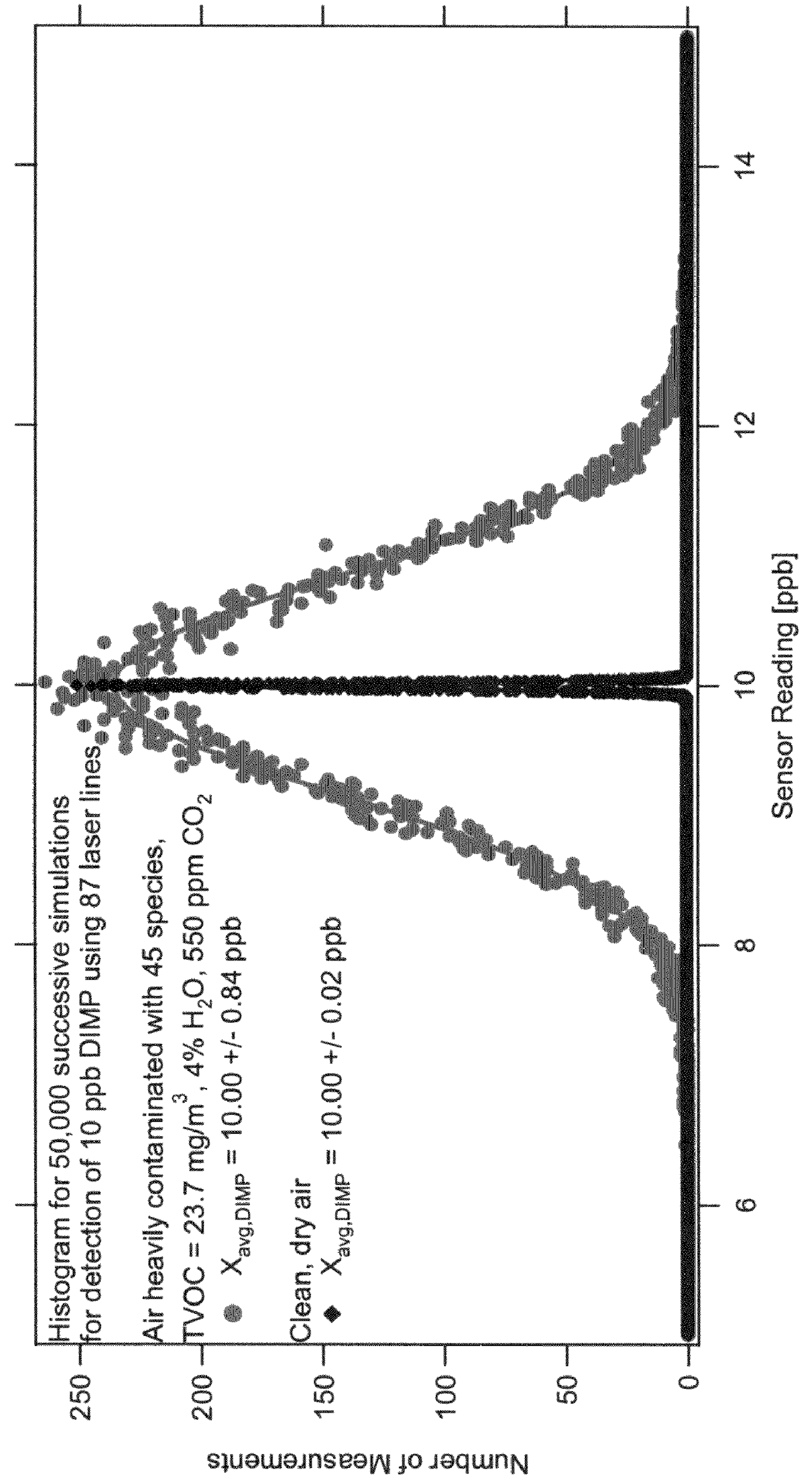
FIG. 4 is a graph of simulations of 10 ppbv DIMP detection in contaminated air overlaid with the results from measurements of DIMP in clean, dry air.

FIG. 4 shows simulations of 10 ppbv DIMP detection in contaminated air overlaid with the results from measurements of DIMP in clean, dry air.

To determine the sensitivity and detection threshold versus PFP (the ROC curve), the simulations must be performed with the interferences present but the target gas absent. The standard deviation of this distribution is the sensitivity. The PFP (for a given threshold) is determined from the same distribution by evaluating how often the sensor mistakenly yields a reading above a predetermined threshold. The simulations with the "worst case" contaminated air and no DIMP, yielded a histogram (FIG. 5, top panel) centered at 0.01 ppbv, with a standard deviation of 850 pptv, which defines the instrument's sensitivity. The PFP at a particular alarm threshold is determined from the histogram as the number of readings above the threshold normalized by the total number of simulations. For example, for a threshold of 1.5 ppbv, the PFP is the ratio of the integrated area under the curve above 1.5 ppbv (shown as $A_1$ on the plot) and the total integrated area (shown as the sum of $A_1$ and $A_2$ on the plot), indicating that 7.7% of the readings will surpass the threshold and thereby falsely set off an alarm. Similarly, for an alarm threshold of 4.15 ppb, only I in every million sensor readings will falsely trigger the alarm when no DIMP is present. And, of course, for an alarm threshold of 0 ppb, all measurements will set off the alarm, yielding a PFP of 100%.

To obtain the ROC curve, i.e., the PFP as a function of different thresholds, the process is repeated for of different alarm levels. The result, plotted in FIG. 6, indicates that as the threshold level increases the PFP decreases rapidly, and for the 4 ppb threshold the PFP reaches the value of ~$10^{-6}$.

Figure 6:
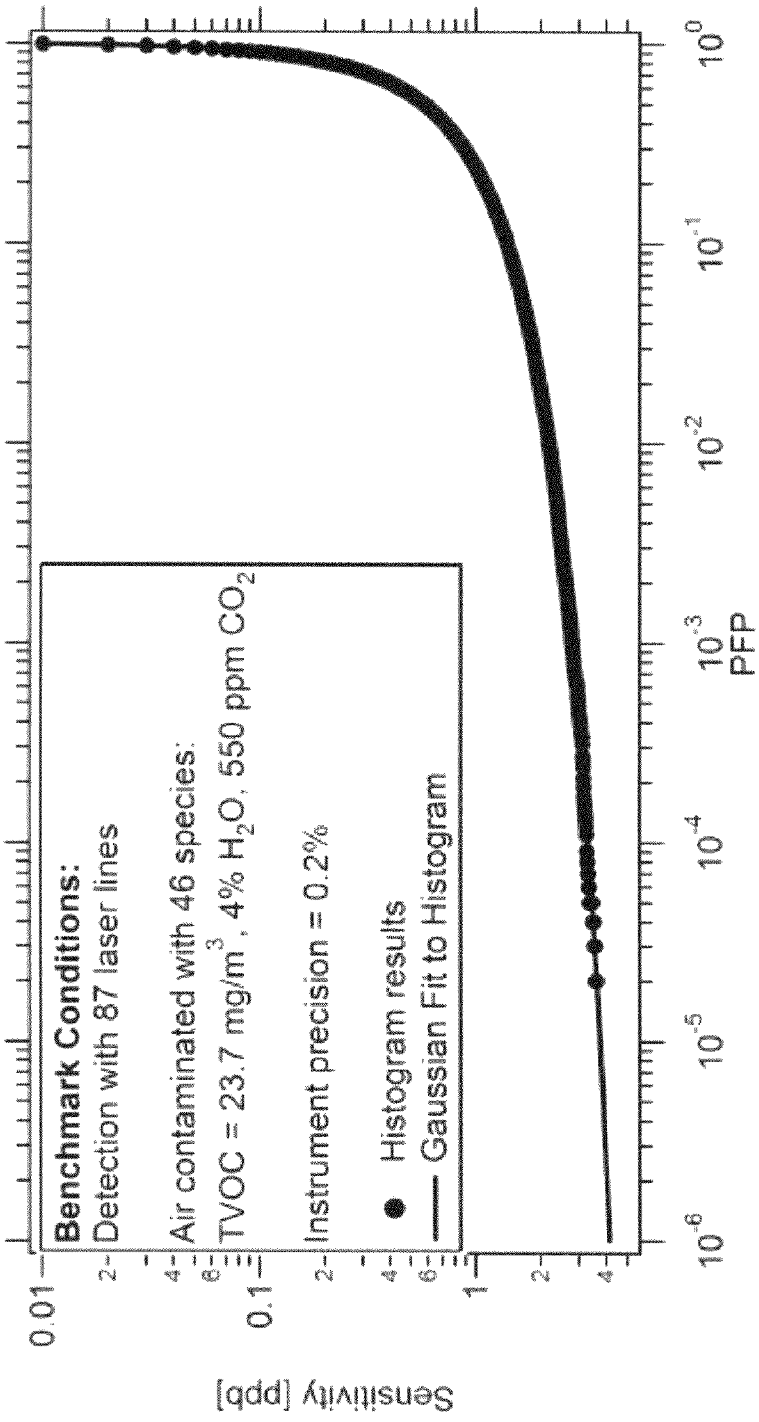
FIG. 6 is a graph of PFP for simulated measurements of 10 ppbv DIMP in heavily contaminated air. A PFP of $1\times10^{-6}$ is achieved for a detection threshold of 4.15 ppb.

FIG. 6 shows the PFP for simulated measurements of 10 ppbv DIMP in heavily contaminated air. A PFP of $1\times10^{-6}$ is achieved for a detection threshold of 4.15 ppb.

To evaluate the sensor PFN, the instrument performance must be modeled when challenging the system with DIMP at a level exceeding the alarm threshold and determining the normalized portion of the histogram below an alarm threshold (area $A_2$ divided by area $A_1+A_2$). In FIG. 5, the bottom panel illustrates PFN calculation for the "worst case" air. With an alarm threshold of 1 ppbv and a challenge of 2 ppbv DIMP, the distribution reveals that 11.3% of the sensor readings will falsely indicate that DIMP is not present.

Figure 7:
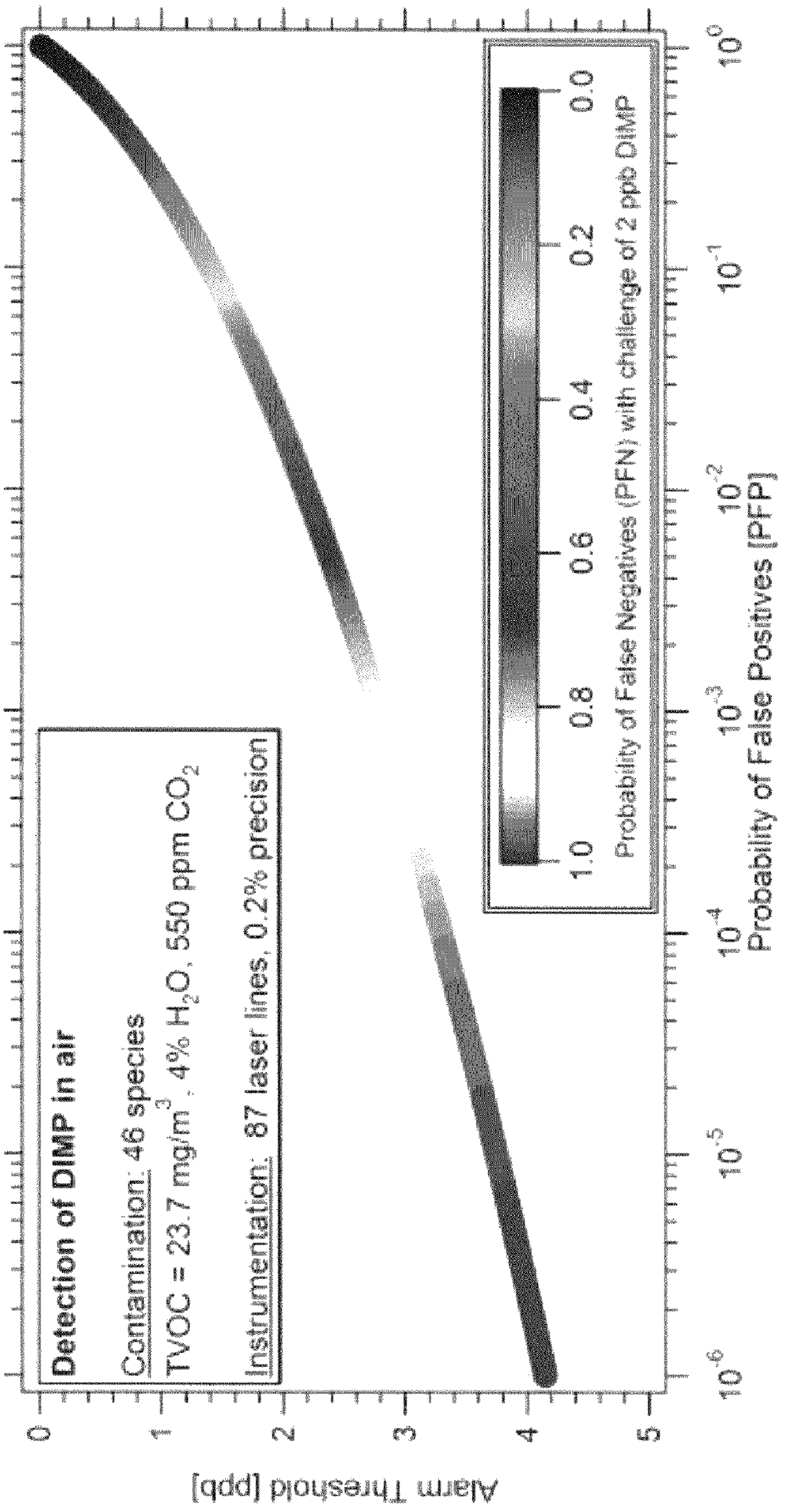
FIG. 7 is a plot of PFP and PFN versus detection threshold obtained from simulations.

By evaluating the PFN at a range of alarm thresholds, the PFP curve from FIG. 6 can be color-coded to reflect PFP and PFN simultaneously, as shown in FIG. 7. Combined display such as the one in FIG. 7 represents an important tool that allows users to specify alarm settings based on the priorities of their applications.

The simulation model provides the tools for exploring ways by which the CWA detection performance may be improved or for testing the limits of the instrument usability in the case of extreme situations. The model has three input parameters: air composition, instrument precision, and laser spectral coverage. Effects of improving the precision of the photoacoustic detection and varying the total volatile organic compound interference load were studied. The effects of varying the spectral coverage are not set forth herein because the tuning range afforded by a $CO_2$ laser is fixed. However, further research regarding such variation in the spectral coverage may yield results similar to those set forth herein.

Figure 8:
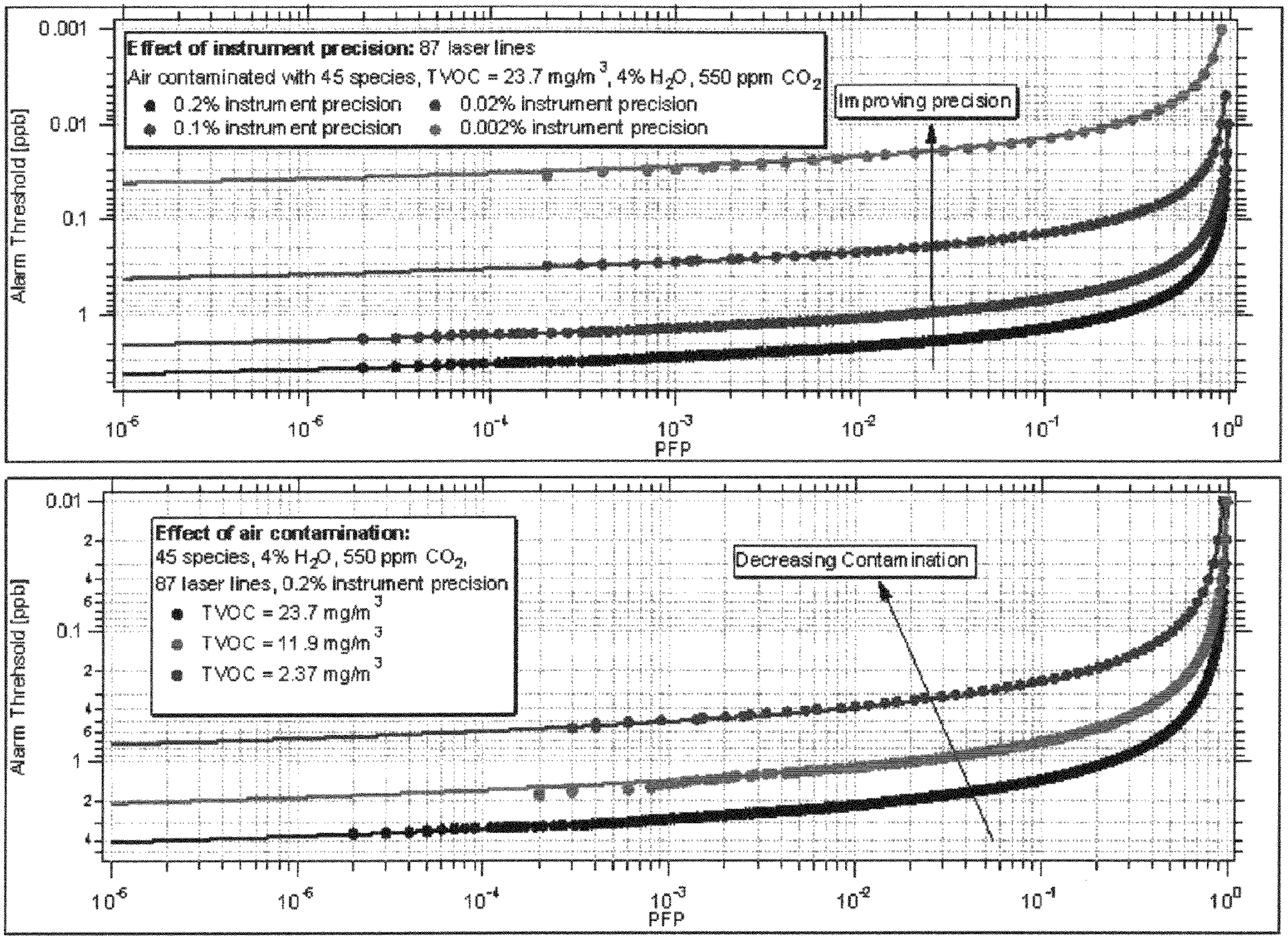
FIG. 8 (top panel) is a graph of simulated ROC curves illustrating improvement in the PFP of L-PAS detection with improving precision of the sensor. The bottom panel is a graph of simulations demonstrating the impact of reducing contamination on the performance of the sensor. Typical indoor air has a total VOC (TVOC) density of <0.5 $mg/m^3$.

As can be deduced from above, limitations to the sensitivity for a desired PFN and PFP comes from the "noise" from the photoacoustic sensor. As described above, the limiting factor for the field deployed L-PAS sensor was its precision, which is the result of the instrument's 10 bit digitizer (9 bits plus sign). The 9 digitization bits give a maximum resolution of 1:512, or approximately 0.002 times the maximum signal for a precision $\beta$=0.2%. By using a sixteen bit digitizer (15 bits plus sign) the resolution can be improved to 1:32,768, yielding $\beta$=0.003%. With this improvement, the noise due to limited precision is still larger than the floor noise, but only by a factor of ten. The improvement in overall system performance that can be obtained by reducing the total noise is shown in FIG. 8 (top panel) which plots the results for different values of precision. For example, an improvement of a factor of 60 in precision (going from a 10 bit digitizer to a 16 bit digitizer) will improve the detection sensitivity by about the same factor, i.e., 60.

In FIG. 8, the bottom panel shows the results of simulations for the worst-case contaminated air, with a total VOC (TVOC) density of 23.7 $mg/m^3$, and for air samples with 2× and 10× less contamination. As the total contamination decreases, the sensor's selectivity improves. For the worst-case contamination, a PFP of $1\times10^{-6}$ can be achieved for a detection threshold of 4.15 ppb. Reducing the contamination by a factor of 10 to 2.37 $mg/m^3$ lowers that threshold to 0.74 ppb.

The problem of sensitively detecting CWAs and TICs in the presence of a realistic array of interferences is set forth in the analysis above by illustrative use of an L-PAS system. An analytical model for optical detection of CWAs and TICs has been developed that can be used for ab initio calculations of L-PAS to determine optimum designs, and was used to evaluate the sensitivity, PFP and PFN. Ultimately, the performance of a L-PAS sensor depends on the availability of high power broadly tunable laser sources, high precision instrumentation, and quantitative spectral libraries.

This L-PAS performance (sensitivity and PFP) can be improved substantially through systematic optimization that includes improvements in the performance of instrument components and design, for example using higher laser output power and tuning range, as well as systematic engineering improvements, such as using better precision A/D converters, transducers, and conditioning electronics.

The approach set forth herein may be used for comparing and optimizing the use of other optical detection technologies for the measurement of CWAs and TICs. The vehicle for the analysis set forth above is the L-PAS. However, the fundamental property measured is the optical absorption. Any other technique that yields the optical absorption signatures, such as long path optical absorption measurements, cavity ring-down spectroscopy or FTIR (Fourier Transform Infrared Spectroscopy) is also equally well described by the analysis presented in this paper. In carrying out the analysis for other modalities of absorption measurements, the photoacoustic signal, S that is directly proportional to the absorption, can be substituted by the actual measured absorption values. The appropriate "noise" for the system must be added to these measurements to derive a stochastically dependent variation of sensitivity with PFP and PFN.

As mentioned above, recent terrorist acts, including the 1995 Sarin attack carried out in a Tokyo subway station by the Aum Shinrikyo cult, have accelerated the search for reliable and sensitive detection of chemical warfare agents to permit a safe and effective evacuation of personnel from buildings and other structures after an attack, to determine safe evacuation perimeters and to evaluate when an attack site is safe to reenter by first responders or other personnel. Moreover, because buildings and public places need 30-60 minutes for evacuation, sensors that can give measurement updates on a minute-by-minute basis while retaining the appropriate sensitivity and selectivity are critical for saving lives and preventing panic.

Figure 9:
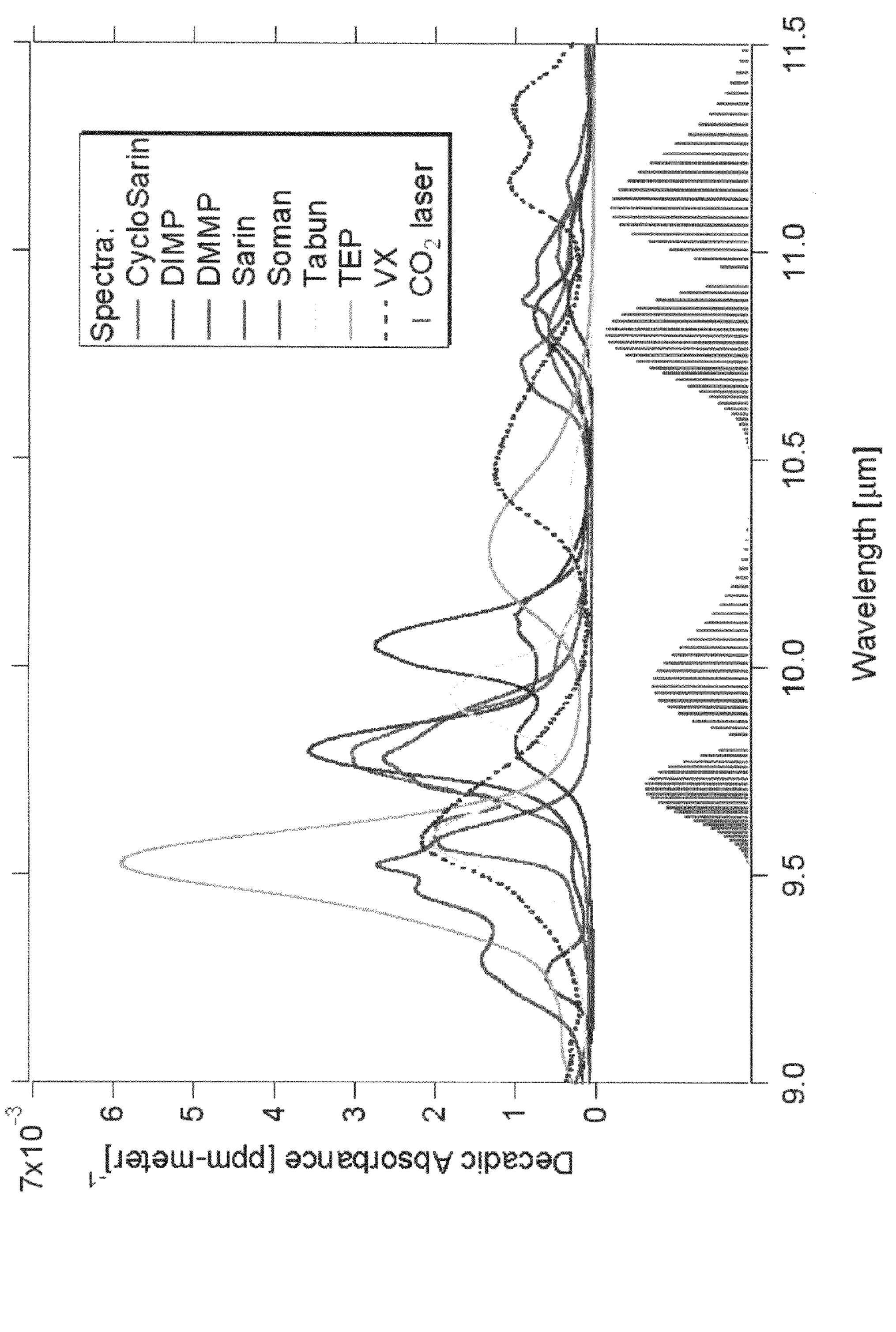
FIG. 9 shows absorption spectra for Tabun (GA), Sarin (GB), Soman (GD), Cyclolsarin (GF), VX, triethyl phosphate (TEP), dimethyl methylphosphate (DMMP) and diisoprophyl methylphosphonate (DIMP) in the 9-11.5 μm region (top panel). The bottom panel features positions and relative power levels of the $^{13}CO_2$ laser output on the lasing transitions as a function of the wavelength.

Optical spectroscopy has long been used for identifying chemical compounds. The CWAs have strong optical absorption features in the infrared in the 9-11.5 μm region (FIG. 9, top panel), with typical decadic absorption strengths 1 of $1\text{-}6\times10^{-3}$ (ppm-meter)$^{-1}$. Despite the relatively large magnitude of the absorption coefficients for these CWAs, for detection at the levels of interest (e.g., 1 ppb), these gases will have a maximum absorption coefficient of $1\text{-}6\times10^{-8}$ $cm^{-1}$. Therefore, ultrasensitive techniques are required. The two most commonly employed are long path measurements and calorimetric methods. Long path absorption measurements include cavity ring down spectroscopy or FTIR with multipass optical cells, both of which use the long pathlengths to compensate for weak absorption coefficients. L-PAS is a typical example of the latter method, which achieves suitable detectivity despite short optical pathlengths due to quiet and sensitive transducers (microphones) and the technique's zero-baseline characteristics. L-PAS has been shown to be a robust technique for weak gas phase optical absorption measurements with minimum detectable absorption coefficients in the range of $10^{-10}$ $cm^{-1}$. Because high power (>1W) $CO_2$ lasers are available with wide tunability (FIG. 9, bottom panel) throughout the 9-11.5 μm where the CWAs absorb, they are ideal laser sources for L-PAS systems for the detection of the CWAs.

However, high sensitivity for detecting small absorptions by itself is not sufficient for detecting CWAs in real environments. A sensor is needed that has very few false alarms. Many trace gas species, normally present in the ambient air, have strong absorption features in the same wavelength region and interfere with the measurements. Obtaining a low probability of false alarms requires effective interference rejection. The problem of interference rejection is severe because the broad absorption features of interferents overlap with the broad absorption features of the target CWA. In normal indoor or outdoor environments, hundreds of gases are present, of which a few dozen need special consideration because of their ambient concentrations, absorption magnitudes, and spectral overlap with the CWAs.

Figure 10:
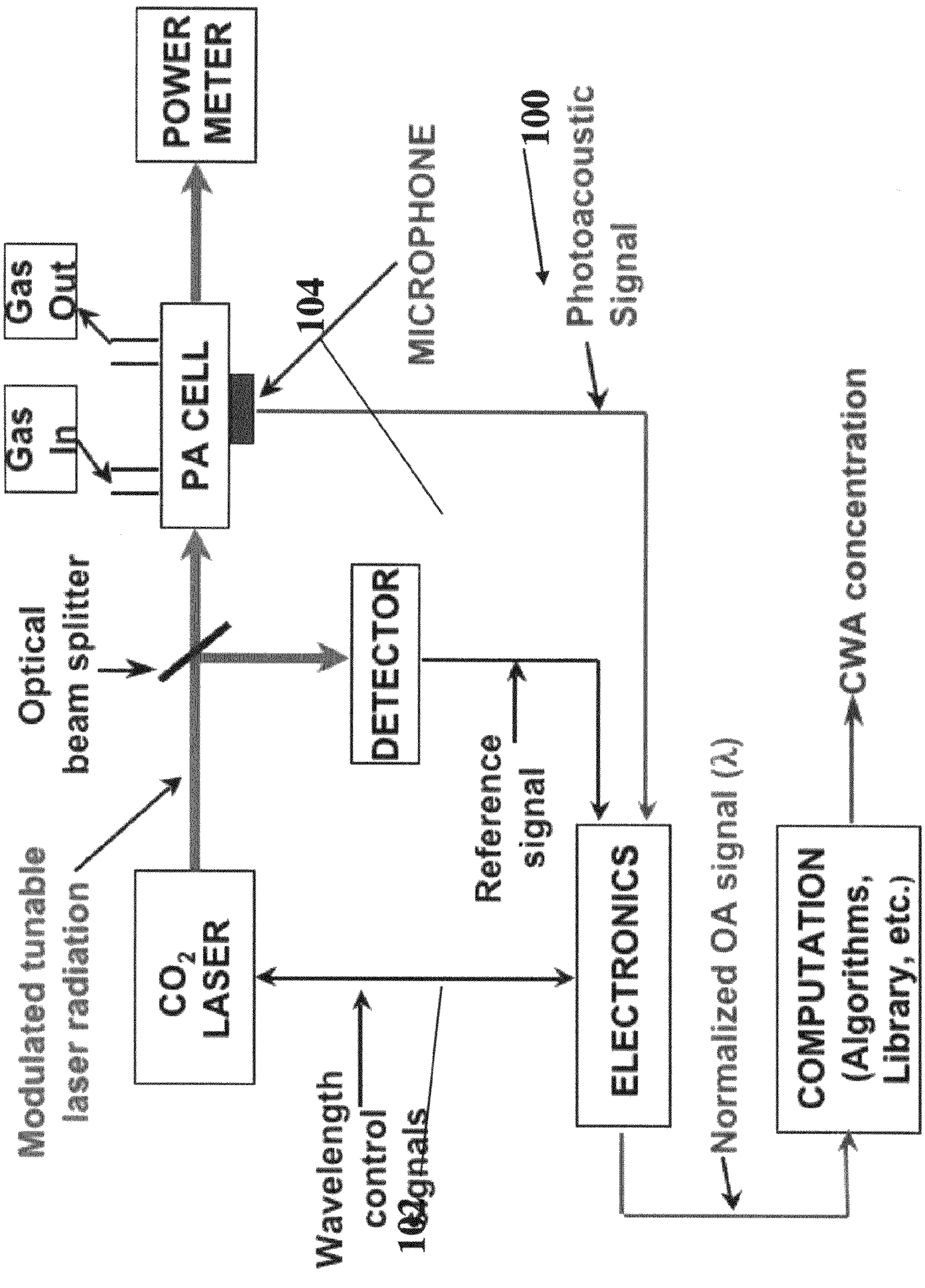
FIG. 10 is a schematic portrayal of an L-PAS analyzer for CWA and other gas detection.

FIG. 10 shows a block diagram of the L-PAS analyzer 100 for the measurements of DIMP in the presence interferents. The photoacoustic spectrometer includes a $^{13}CO_2$ laser 102 that is tuned across 34 transitions in the P and R branches of the $00^01\text{-}[10^00, 02^00]_{11}$ band, covering 9.6 μm to 10.2 μm in ~40 seconds. The normalized photoacoustic signal on a transition is proportional to the cumulative optical absorption caused by all of the gases present in the cell 104 including DIMP. The individual contribution from DIMP and the other species is extracted using a linear (or possibly other) pattern recognition algorithm along with the spectral libraries recorded with the spectrometer. The L-PAS sensor was calibrated by introducing into the cell known concentrations of DIMP (see FIG. 11, bottom left panel).

Figure 11:
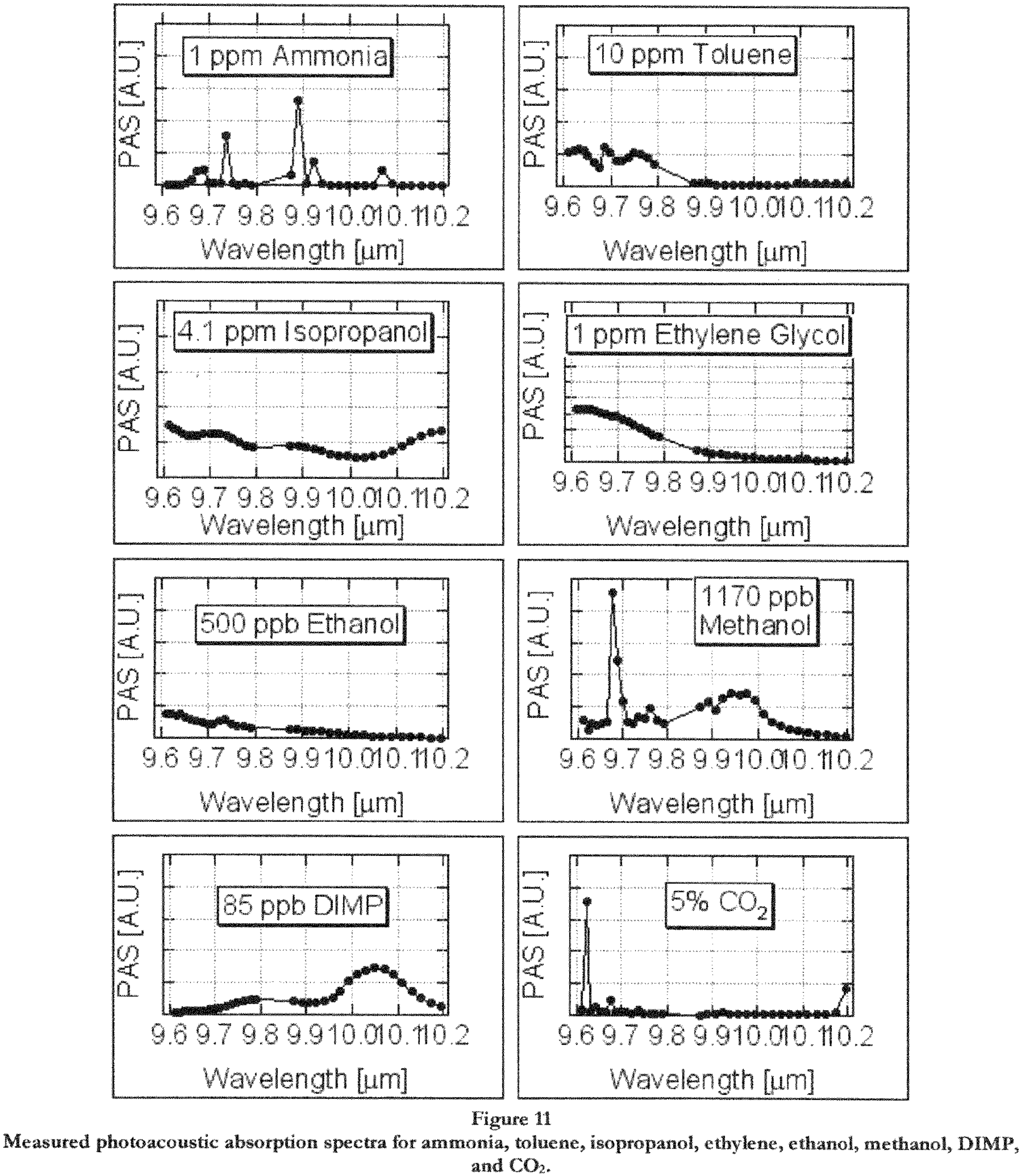
FIG. 11 are graphs of measured photoacoustic absorption spectra for ammonia, toluene, isopropanol, ethylene, ethanol, methanol, DIMP, and $CO_2$.

FIG. 11 shows exemplary spectral libraries used to evaluate $\alpha_{i,\lambda_j}$, the absorption coefficient of species i at wavelength $\lambda_j$. Three additional vectors were added to account for the offset, slope and curve of the background signals. When a mixture of trace gases is present in the photoacoustic cell, the total absorption, $\alpha_{\lambda_j}$, at a specific wavelength, $\lambda_j$, is given (as above) by $$\text{Absorption Coefficient}|_{\lambda_j} = \alpha_{\lambda_j} = \sum_{i=1}^{\#of\ species} \alpha_{i,\lambda_j} = \sum_{i=1}^{\#of\ species} \sigma_{i,\lambda_j} X_i \quad (2)$$

where $\sigma_{i,\lambda_j}$ is the absorbance for species i at wavelength $\lambda_j$, and $X_i$ is the mole fraction of the species i. The signal is linear for over five orders of magnitude until the cumulative optical density approaches 6% or greater, and the combined absorbance at any particular wavelength is a linear combination of different contributing absorbers. Finally, from the measured absorption matrix, $\alpha_{i,\lambda_j}$, the concentration of the specific component is derived.

A series of measurements were carried out to assess the capability of the L-PAS analyzer to measure DIMP in the presence of eight species that were determined to be the worst expected interferents: water, carbon dioxide, propanol, ethylene glycol, toluene, methanol, ammonia and ethanol. The analyzer's capability is a combination of its sensitivity and selectivity (low false alarms when DIMP is not present). Four different measurement scenarios were used: (1) 0 ppb DIMP in synthetic clean air to determine best-case sensitivity; (2) 0 ppb DIMP in real outdoor Santa Monica, Calif. air to establish a benchmark for sensitivity and selectivity in nominal urban conditions; (3) 0 ppb DIMP in synthetic, highly contaminated air to establish sensitivity and selectivity under extreme conditions; and (4) 14.3 ppb DIMP in synthetic contaminated air to establish accuracy.

Figure 12:
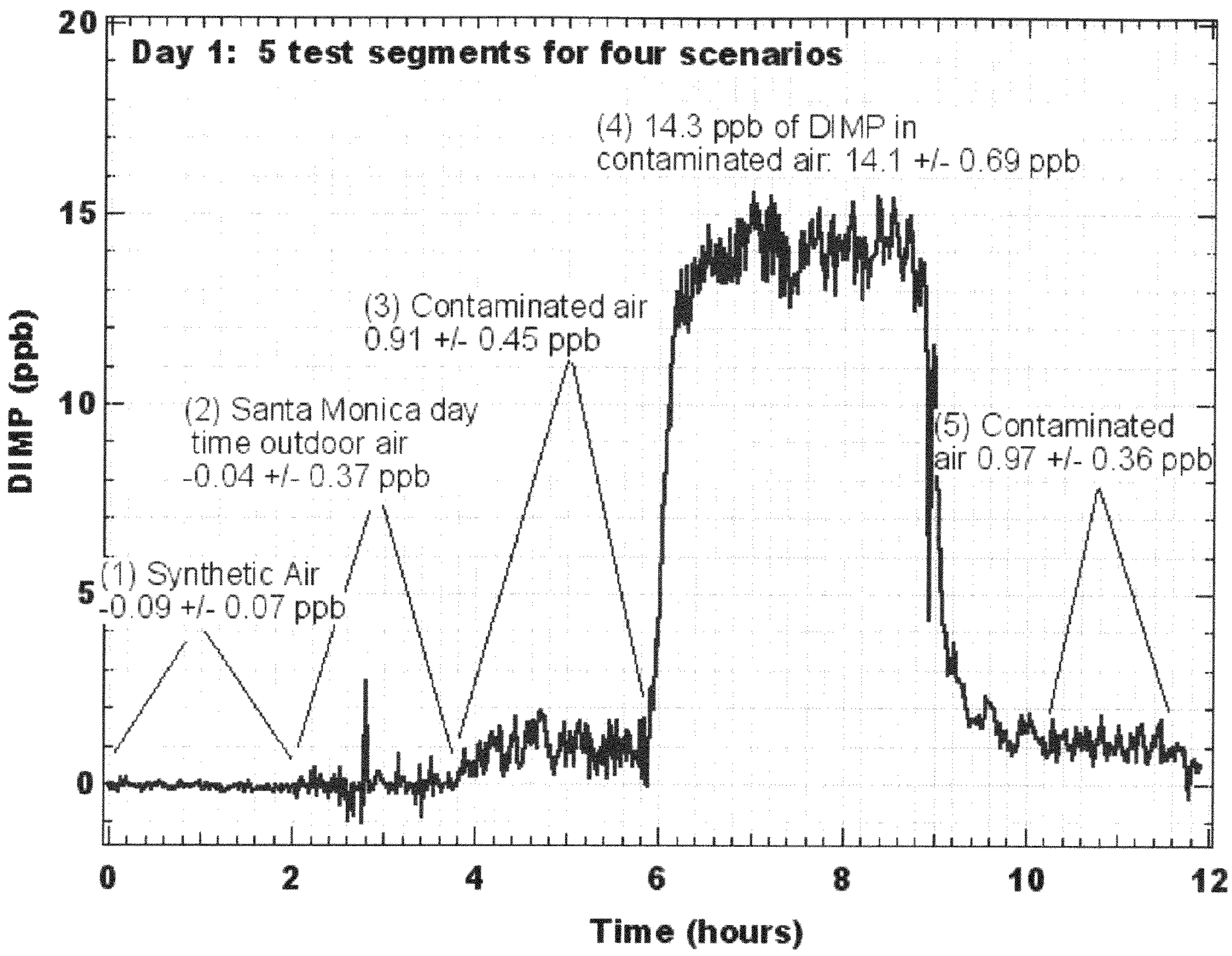
FIG. 12 is a graph of L-PAS analyzer measurements for: 1) synthetic clean air, 2) Santa Monica city street air, 3) synthetic contaminated air no DIMP, 4) synthetic contaminated air with 14.3 ppb DIMP present, and 5) synthetic contaminated air with no DIMP.

The component gases and concentrations for each case are listed in Table 4. The results of these four test cases are plotted in FIG. 12 with five different test segments (Case 3 is conducted twice), and summarized in Table 5. This case is used to establish a benchmark for sensitivity with synthetic clean air ($O_2$, $N_2$, 1% $H_2O$, 500 ppm $CO_2$) and no DIMP present. For this case, the analyzer produced a reading of –0.09 ppb DIMP with a I a replicate precision of 0.07 ppb over approximately 120 successive measurements (see the first segment of FIG. 5). Thus, the best-case sensitivity for the system is approximately 70 ppt (0.51 $\mu g/m^3$) and the zero-level is within 100 ppt of true zero.

TABLE 4

Gas components and concentrations used in the present study for synthetic clean air (second column), outdoor Santa Monica air (third column), and synthetic contaminated air (fourth column).

| Component | Concentrations for Synthetic Clean Air | Concentrations for Santa Monica Air | Concentrations for Synthetic Contaminated Air |
|---|---|---|---|
| Nitrogen | 79% | 79% | 79% |
| Oxygen | 20% | 20% | 20% |
| Water | 1% | 1-2% | 1% |
| Carbon Dioxide | 500 ppm | 300-550 ppm | 500 ppm |
| n-propanol | None | Unknown | 730 ppm |
| Ethylene Glycol | None | Unknown | 360 ppm |
| Toluene | None | Unknown | 3.6 ppm |
| Methanol | None | Unknown | 850 ppb |
| Ammonia | None | Unknown | 700 ppb |
| Ethanol | None | Unknown | 330 ppb |
| All others | None | Unknown | None |

TABLE 5

Results for each test segment

| Segment | Test Conditions | Actual DIMP Concentration | Measured DIMP Concentration |
|---|---|---|---|
| ① | Synthetic Clean Air | 0 ppb | −0.09 ± 0.07 ppb |
| ② | Santa Monica Outdoor Air (day time) | 0 ppb | −0.04 ± 0.37 ppb |
| ③ | Synthetic Contaminated Air | 0 ppb | 0.91 ± 0.45 ppb |
| ④ | Synthetic Contaminated Air | 14.3 ppb | 14.1 ± 0.69 ppb |
| ⑤ | Synthetic Contaminated Air | 0 ppb | 0.97 ± 0.36 ppb |

Testing the L-PAS system 100 under nominal contamination levels conditions was achieved in case 2 by measuring daytime outdoor Santa Monica air with no DIMP present (Table 4). For these tests (segment 2 of FIG. 12) approximately 110 successive measurements yielded a reading of –0.04 ppb DIMP with a 1σ replicate precision of 0.37 ppb (2.7 $\mu g/m^3$). The cumulative effect of the interferences is a degradation of the sensitivity by a factor of ~6, but with no effect on the zero level, which remained within 100 ppt of true zero.

A controlled sensitivity test in highly contaminated conditions was conducted by creating a synthetic air mixture (Table 4), the components of which are expected to be significant interferences. The concentration for each species was picked to be at levels exceeding those expected to be found in indoor contaminated air. The results, shown in the segments 3 and 5 (FIG. 12) reveal that for the synthetic contaminated air, the interferences cause the zero-level increase to an average reading of 0.91 and 0.97 ppb DIMP for the two respective segments, and degrade the 1σ replicate precision to 0.45 and 0.36 ppb (3.3 and 2.7 $\mu g/m^3$), respectively. For reference, a typical CWA (Sarin) exposure that causes the first noticeable health effect (miosis) is 1 $mg.min/m^3$, i.e., a permissible concentration 10-12 of about 33 $\mu g/m^3$ (5.8 ppb) for a 30 minutes exposure and 16 $\mu g/m^3$ (2.9 ppb) for a 60 minute exposure. Thus, the sensitivities obtained in these studies are well suited for safeguarding populations in an urban setting.

The L-PAS accuracy in the presence of interferences was established in case 4, where 14.3 ppb of DIMP was added to the synthetic contaminated air mixture. The L-PAS analyzer yielded an average reading of 14.1±0.69 ppb (segment 4, FIG. 12) yielding a relative accuracy better than 2% and a precision better than 5%.

Figure 13:
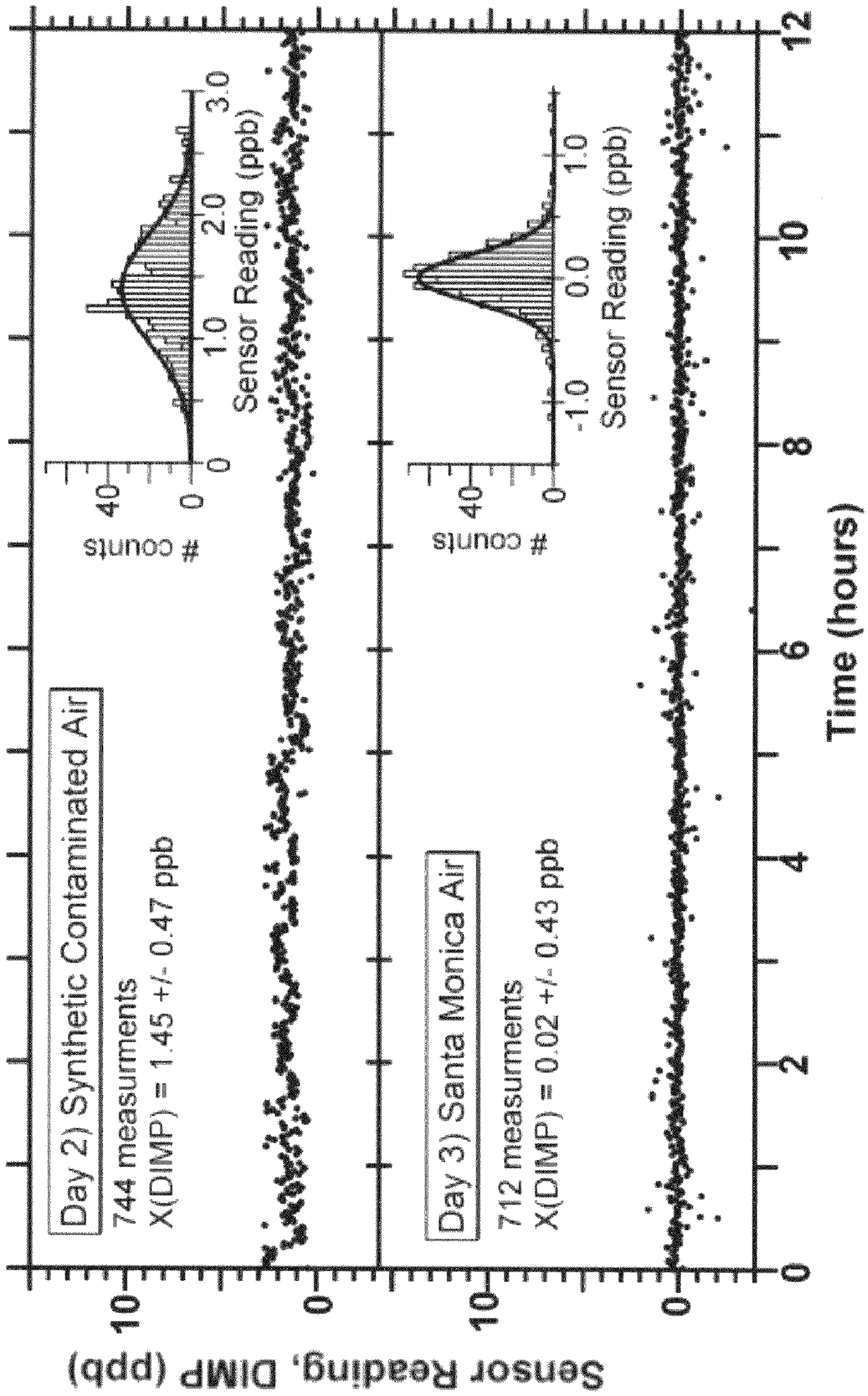
FIG. 13 is a sensory reading of measurements of DIMP in synthetic contaminated air and Santa Monica air over 12 hours on different days to determine the sensitivity of PFP.

The data for apparent DIMP values when it is not present permits an estimate of the PFP for a particular alarm threshold (sometimes referred to as the sensitivity). The PFP is the number of times the sensor indicates that DIMP is present above the alarm threshold even when no DIMP is present. The PFP is evaluated using the statistical noise characteristics of the observed "zero DIMP" signal. The statistical variation of sensor readings over 12 hours of successive measurements for the cases 2 and 3 are shown in FIG. 13. The average sensor reading in synthetic contaminated air over the 12-hour period on Day 2 was 1.45 ppb with a standard deviation of 0.47 ppb (the offset is the result of interferences, rather than from residual DIMP). The average measurements in Santa Monica outdoor air over the 12-hour period on Day 3 was 0.02 ppb with a standard deviation of 0.43 ppb, again achieving a zero value within 100 ppt of true zero.

Each case has over 700 measurements, and the measurement histograms are shown as insets. The PFP is calculated by performing a Gaussian fit to the histograms and then comparing the area under the curve above the alarm level with the total area under the curve. For the case of synthetic contaminated air, a false alarm will occur once for every million measurements if the alarm threshold is set for 3.0 ppb, while for the Santa Monica outdoor air a PFP of 1:106 is achieved with a threshold of 1.2 ppb. Because the measurement duration is approximately one minute, a PFP of 1:106 corresponds to one false alarm approximately every 23 months. Both of these alarm settings are better than the 30 minute exposure threshold for miosis (33 μg/$m^3$ or 5.8 ppb), and are satisfactory for the 60 minute threshold (16 μg/$m^3$ or 2.9 ppb). This level of PFP should be acceptable for general application to warn the population about a CWA attack, with sufficient time to evacuate the attack site before miosis exposure threshold is exceeded.

In conclusion, an innovative L-PAS technique is very suitable for sensing the presence of DIMP, a CWA nerve gas surrogate, in the presence of interferences in outdoor air and synthetic contaminated air. The analyzer's sensitivity of 70 ppt in clean air and better than 450 ppt in nominal outdoor air and synthetic contaminated air easily meet the requirements for protecting personnel from terrorist CWA attacks even in urban settings.

While the present invention has been described with regards to particular embodiments, it is recognized that additional variations of the present invention may be devised without departing from the inventive concept. The gas detection systems and methods disclosed herein provide several goals, not the least of which are the detection of gases in a precise and accurate manner, but also in a manner that is reliable and from a device that could be very portable and easy to use. These and other objects and advantages of the present invention will be apparent from a review of the foregoing specification and accompanying drawings. The foregoing objects are some of but a few of the goals sought to be attained by the present invention.

What is claimed is:

1. A gas detector, comprising:

an optical analyzer detecting in a sample of gas optical absorbance of said sample at a plurality of wavelengths, said optical analyzer transmitting an absorbency signal representative of optical absorbency for each respective one of said plurality of wavelengths;

said optical analyzer having a selectable sensitivity;

said selectable sensitivity selected according to a first probability that said optical analyzer will transmit a false positive (PFP) signal for a first gas and a second probability that said optical analyzer will transmit a false negative PFN signal for said first gas;

a spectral library of gas species absorbing one or more of said plurality of wavelengths including determined absorptions for expected gases and target gases; and a processor receiving said absorbency signals and applying pattern recognition with said absorbency signals and said determined absorptions to provide mole fraction quantities for said expected gases and said target gases; whereby said sample of gas may be analyzed for presence and quantity of expected gases and target gases.

2. A gas detector as set forth in claim 1, further comprising:

said optical analyzer including an optical analyzer selected from the group consisting of: tunable laser systems, laser photoacoustic detection systems (L-PAS); long path optical absorption measuring systems, cavity ring-down spectroscopy systems, FTIR systems, and any combinations thereof.

3. A gas detector as set forth in claim 1, further comprising:

said optical analyzer including a L-PAS system using a $CO_2$ laser.

4. A gas detector as set forth in claim 1, further comprising:

said optical analyzer including a L-PAS using one or several tunable quantum cascade lasers.

5. A gas detector as set forth in claim 1, further comprising:

said optical analyzer including a L-PAS using a tunable parametric oscillator.

6. A gas detector as set forth in claim 1, further comprising:

said optical analyzer including a L-PAS using one or several direct bandgap recombination type semiconductor lasers.

7. A gas detector as set forth in claim 1, further comprising:

said optical analyzer including a L-PAS using any combination of $CO_2$ lasers, quantum cascade lasers, parametric oscillators, and direct bandgap recombination type semiconductor lasers.

8. A gas detector as set forth in claim 1, further comprising:

said plurality of wavelengths being equal or greater in number than the number of absorbing gas species.

9. A gas detector as set forth in claim 1, further comprising:

said spectral library derived from optical analysis of said expected gases and said target gases by said optical analyzer.

10. A gas detector as set forth in claim 1, further comprising:

said pattern recognition algorithms including use of a least squares fitting technique.

11. A gas detector, comprising:

an optical analyzer detecting in a sample of gas optical absorbance of said sample at a plurality of wavelengths, said optical analyzer transmitting an absorbency signal representative of optical absorbency for each respective one of said plurality of wavelengths, said optical analyzer selected from the group consisting of:

tunable laser systems;

laser photoacoustic systems including a L-PAS system using a $CO_2$ laser;

long path optical absorption measuring systems;

cavity ring-down spectroscopy systems;

FTIR systems;

a L-PAS using one or several tunable quantum cascade lasers;

a L-PAS using a tunable parametric oscillator;

a L-PAS using one or several direct bandgap recombination type semiconductor lasers;

a L-PAS using any combination of $CO_2$ lasers, quantum cascade lasers, parametric oscillators, and direct bandgap recombination type semiconductor lasers; and any combinations thereof;

said optical analyzer having a selectable sensitivity;

said selectable sensitivity selected according to a first probability that said optical analyzer will transmit a false positive (PFP) signal for a first gas and a second probability that said optical analyzer will transmit a false negative (PFN) signal for said first gas;

a spectral library of gas species absorbing one or more of said plurality of wavelengths including determined absorptions for expected gases and target gases, said spectral library derived from optical analysis of said expected gases and said target gases by said optical analyzer; said plurality of wavelengths of said optical analyzer being equal or greater in number than the number of absorbing gas species; and a processor receiving said absorbency signals and applying a least squares fitting technique with said absorbency signals and said determined absorptions to provide mole fraction quantities for said expected gases and said target gases; whereby said sample of gas may be analyzed for presence and quantity of said expected gases and said target gases.

12. A method for detecting gases, comprising:

providing an optical analyzer which transmits a signal proportional to optical absorbance;

determining a first probability that said optical analyzer will transmit a false positive (PFP) signal for a first gas;

determining a second probability that said optical analyzer will transmit a false negative (PFN) signal for said first gas;

selecting a sensitivity for said optical analyzer according to said PFP and PFN;

providing a gas sample to be tested;

analyzing said gas sample with said optical analyzer to obtain an absorbency signal analyzing said absorbency signal in conjunction with a spectral library of determined absorptions for expected gases and target gases; and determining mole fractions of said expected gases and said target gases; whereby said gas sample may be analyzed for presence and quantity of expected gases and target gases.

13. A method for detecting gases as set forth in claim 12, further comprising:

wherein said optical analyzer includes an optical analyzer detecting in a sample of gas optical absorbance of said sample at a plurality of wavelengths, said optical analyzer transmitting said absorbency signal representative of optical absorbency for each respective one of said plurality of wavelengths.

14. A method for detecting gases as set forth in claim 13, further comprising:

said spectral library includes a spectral library of gas species absorbing one or more of said plurality of wavelengths including determined absorptions for expected gases and target gases.

15. A method for detecting gases as set forth in claim 13, further comprising:

said step of analyzing said absorbency signal and said step of determining mole fractions achieved by providing a processor receiving said absorbency signals and applying pattern recognition with said absorbency signals and said determined absorptions to provide mole fraction quantities for said expected gases and said target gases.

16. A method for detecting gases as set forth in claim 12, further comprising:

said gas sample being a sample of ambient or other air.

* * * * *